(12) United States Patent
Barlos

(10) Patent No.: US 8,785,384 B2
(45) Date of Patent: Jul. 22, 2014

(54) PEPTIDE SYNTHESIS

(75) Inventor: Kleomenis K. Barlos, Patras (GR)

(73) Assignee: Chemical & Biopharmaceutical Laboratories of Patras (GR)

( * ) Notice: Subject to any disclaimer, the term of this patent is extended or adjusted under 35 U.S.C. 154(b) by 0 days.

(21) Appl. No.: 12/783,223

(22) Filed: May 19, 2010

(65) Prior Publication Data

US 2011/0039778 A1 Feb. 17, 2011

(51) Int. Cl.
*A61K 38/16* (2006.01)
*A61P 21/02* (2006.01)

(52) U.S. Cl.
USPC ............................................ 514/12.1

(58) Field of Classification Search
None
See application file for complete search history.

(56) References Cited

U.S. PATENT DOCUMENTS

| | | | | |
|---|---|---|---|---|
| 4,835,251 A | * | 5/1989 | Burnier et al. | 530/324 |
| 5,053,488 A | * | 10/1991 | Hudson et al. | 530/324 |
| 2005/0032683 A1 | * | 2/2005 | Amento et al. | 514/12 |
| 2008/0051336 A1 | * | 2/2008 | Bonaventure et al. | 514/12 |

FOREIGN PATENT DOCUMENTS

| GR | 1006759 B2 | 4/2010 |
|---|---|---|
| WO | WO 9500645 A2 | 1/1995 |

OTHER PUBLICATIONS

Bullesbach and Schwabe, J. Biol. Chem. 266: 10754-10761, 1991.*
Bullesbach and Schwabe, J.Biol.Chem. 275: 35276-35280, 2000.*
Liu et al., Pharmaceutical Res. 15: 632-640, 1998.*
Brot et al., 1998 (abstract only), 1 page.*
Samuel et al., Kidney International 65:2054-2064, 2004.*
XP 009138962, Feb. 26, 2010, Barlos, Kostas L. et al.
XP 002603133, Apr. 20, 2010, Barlos, Kleomenis et al.
Bullesbach E E et al., "Total Synthesis of Human Relaxin and Human Relaxin Derivatives by Solid-Phase Peptide Synthesis and Site-Directed Chain Combination", Journal of Biological Chemistry, American Society for Biochemistry and Molecular Biology, Inc., US, Jan. 1, 1991, pp. 10754-10761, vol. 266, No. 17.
Samuel C S et al., "Drugs of the Future: The Hormone Relaxin", CMLS Cellular and Molecular Life Sciences, Birkhauser-Verlag, BA LNKD, Apr. 27, 2007, pp. 1539-1557, vol. 64, No. 12.
A. H. MacLennan et al, The Journal of Reproductive Medicine, vol. 40, No. 10, 703-706, 1995.

* cited by examiner

*Primary Examiner* — Gyan Chandra
(74) *Attorney, Agent, or Firm* — Sam L. Nguyen; Hamilton Desanctis & Cha, LLP

(57) ABSTRACT

A process for producing an insulin type peptide, for example a relaxin, involving oxidizing a methionine residue on a B-chain having cysteine residues and combining the B chain with an A chain having cysteine residues to form a peptide having intermolecular disulphide links and biological activity. Novel synthetic relaxin 1 and methionine oxidized relaxins and Met(O) B-chains having enhanced solubility are disclosed.

10 Claims, 17 Drawing Sheets

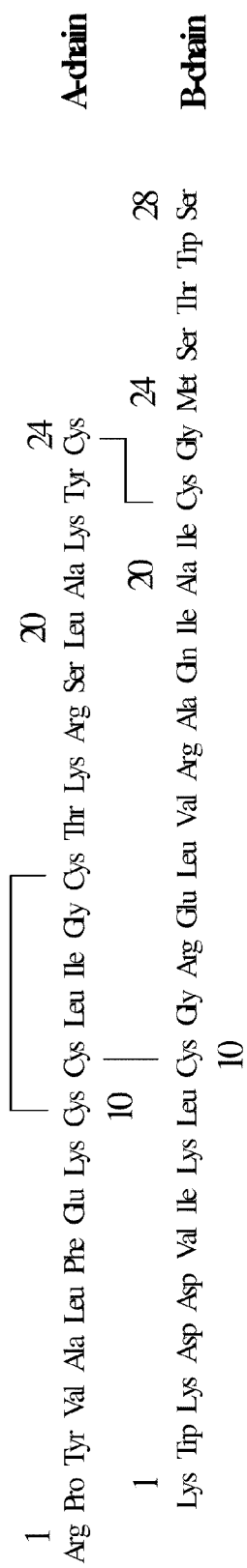
Figure 1. Structure (sequence) of synthetic human Relaxin 1 (shRLX1)
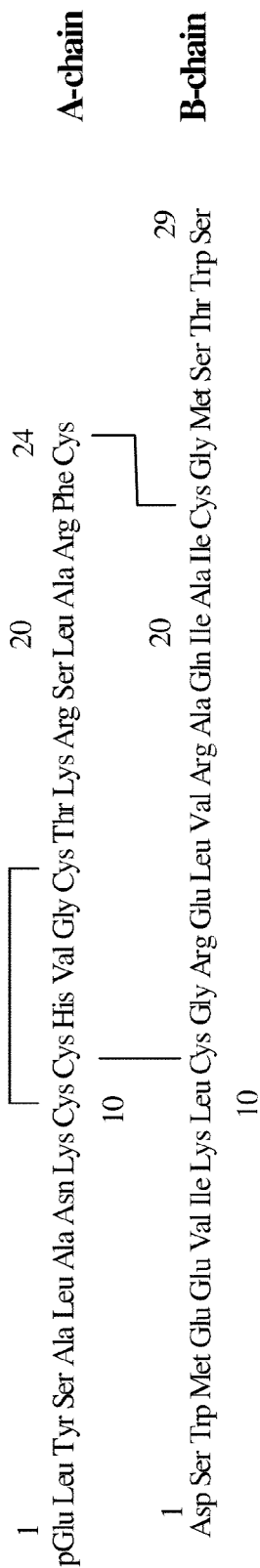
Figure 2. Structure (sequence) of synthetic human Relaxin 2 (shRLX2)

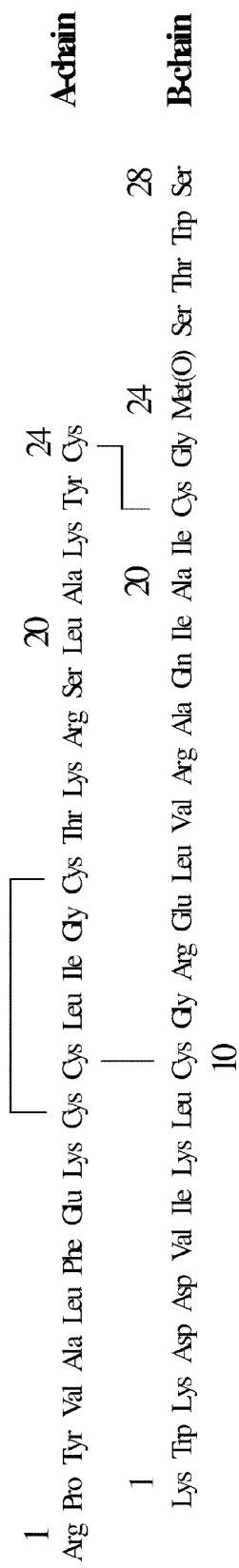
Figure 3. Structure (sequence) of B-Met(O)²⁴- synthetic human Relaxin 1 ( B-Met(O)²⁴-shRLX1)
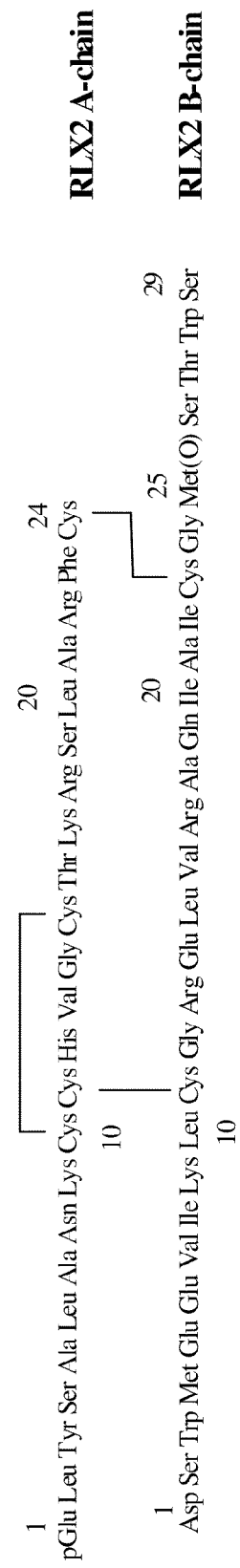
Figure 4. Structure (sequence) of synthetic human Met(O)²⁵-Relaxin 2 [(Met(O)²⁵-RLX2]

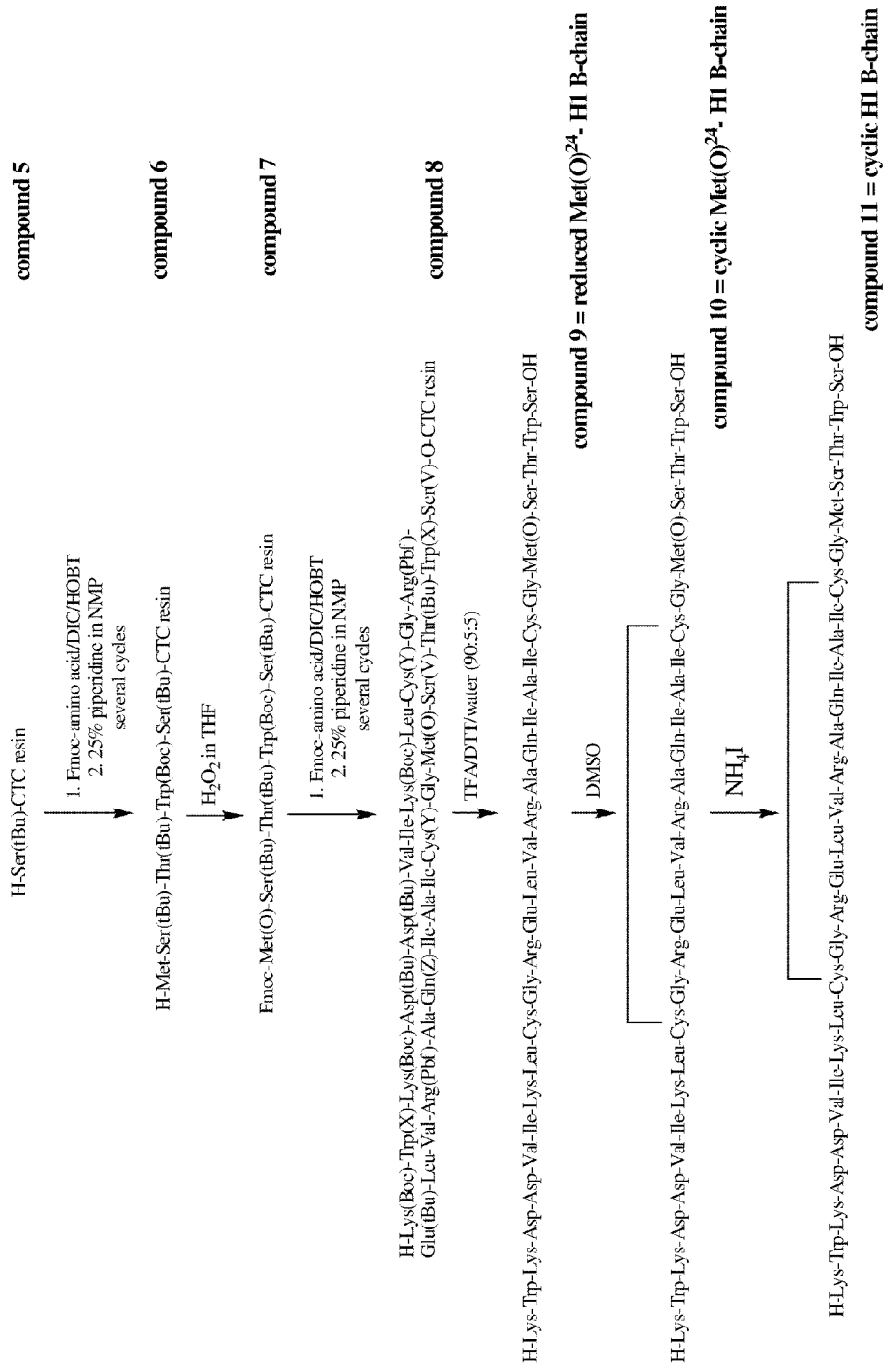
Figure 5. DMSO oxidation; Synthesis of reduced (linear) Met(O)$^{24}$-human Relaxin 1 B-chain [compound 9, Met(O)$^{24}$-shRLX1B], of oxidized (cyclic) Met(O)$^{24}$-human Relaxin 1 B-chain [compound 10, Met(O)$^{24}$-shRLX1B] and of oxidized (cyclic) human Relaxin 1 B-chain [compound 11, shRLX1B]

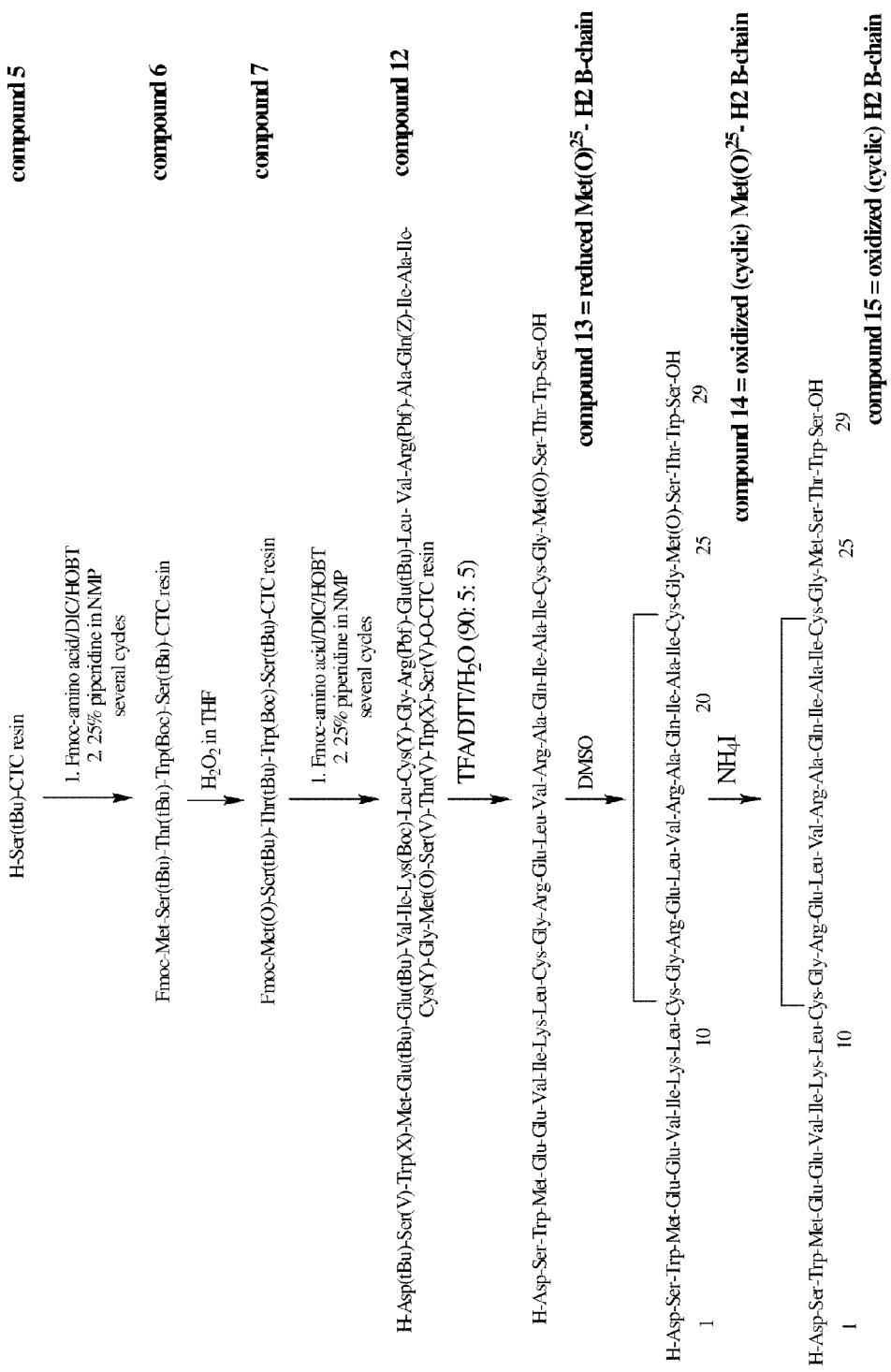
Figure 6. DMSO oxidation; Synthesis of reduced (linear) Met(O)$^{25}$-human Relaxin 2 B-chain [compound 13, Met(O)$^{25}$-shRLX2B], of oxidized (cyclic) Met(O)$^{25}$-human Relaxin 2 B-chain [compound 14, Met(O)$^{25}$-shRLX2B] and of oxidized (cyclic) human Relaxin 2 B-chain [compound 15, shRLX2B]

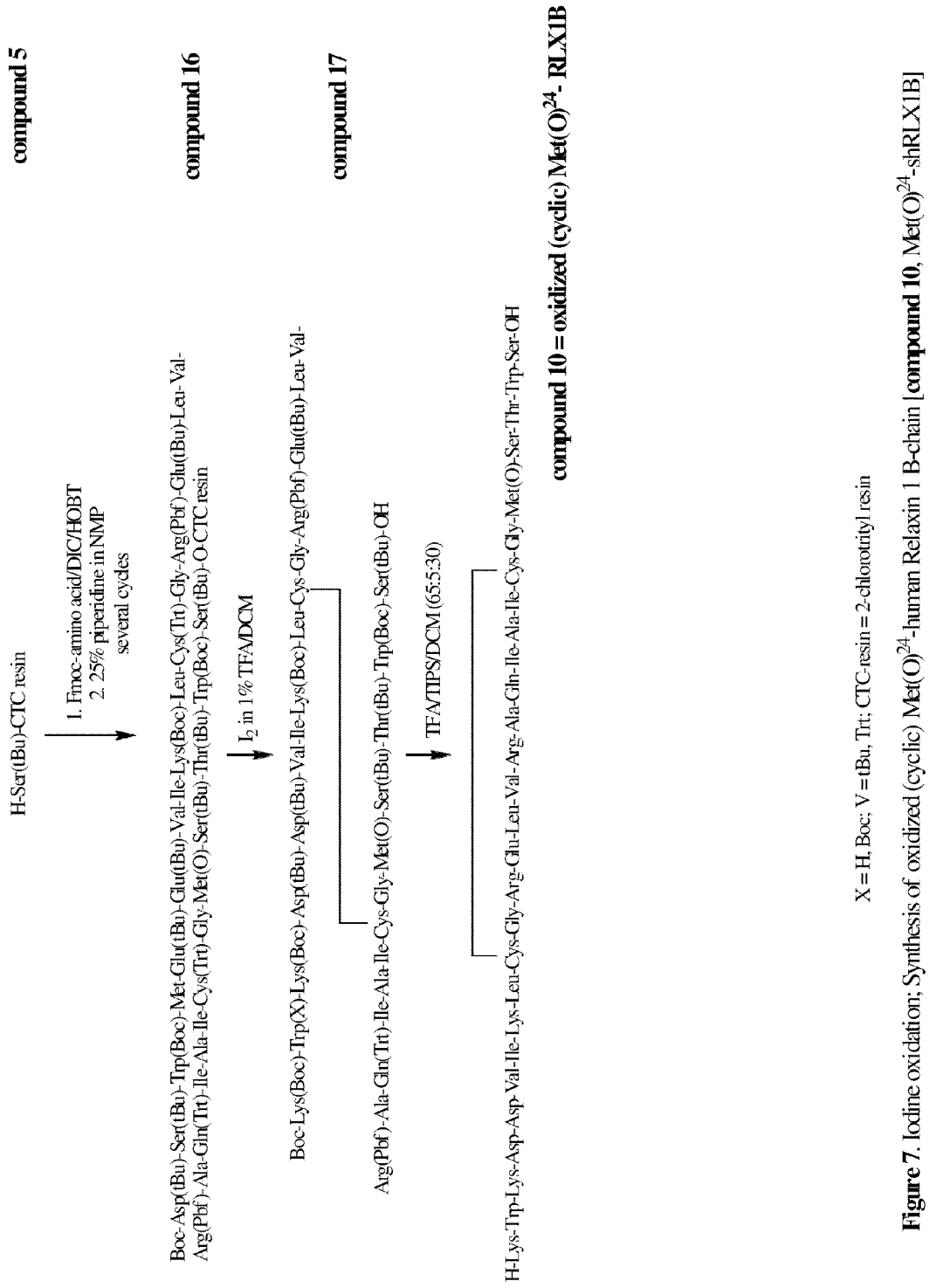
Figure 7. Iodine oxidation; Synthesis of oxidized (cyclic) Met(O)$^{24}$-human Relaxin 1 B-chain [compound 10, Met(O)$^{24}$-shRLX1B]

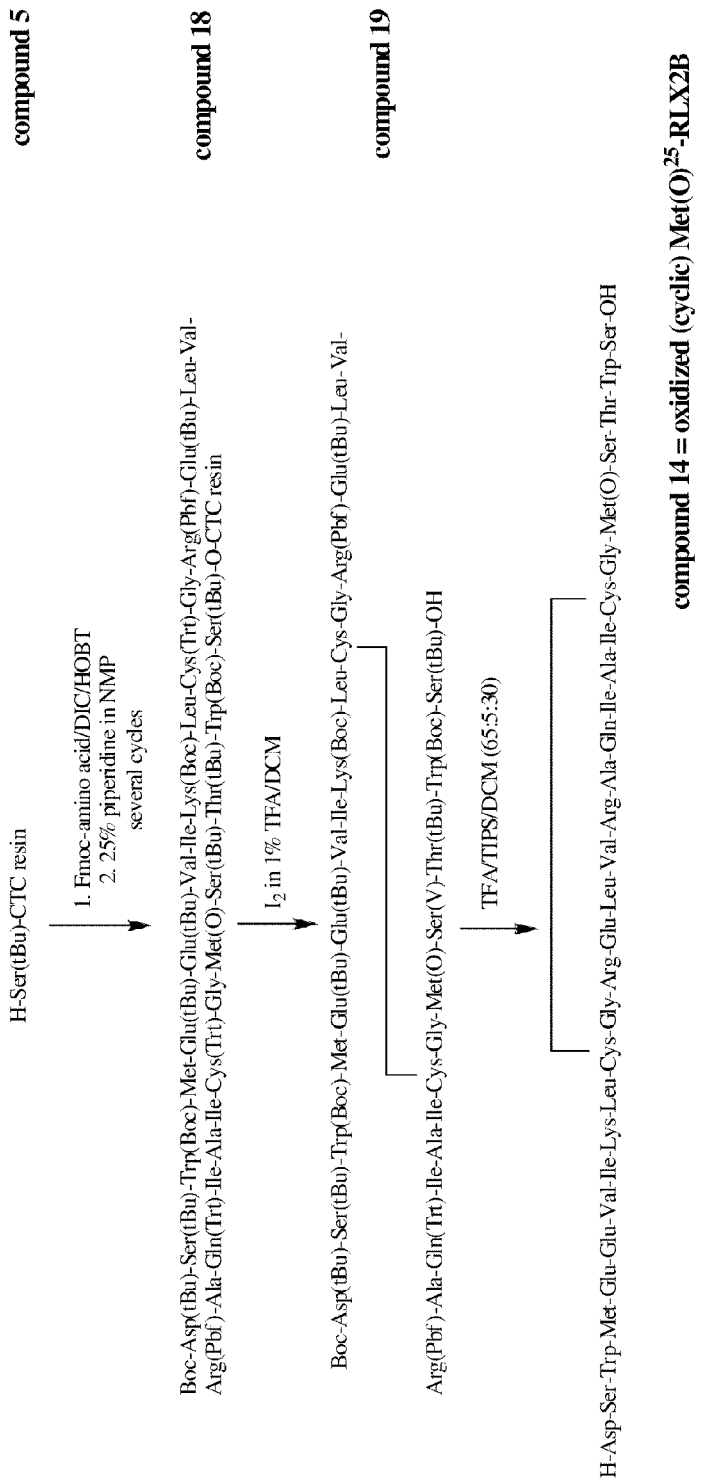
Figure 8. Synthesis of oxidized (cyclic) Met(O)25-human Relaxin 2 B-chain [Met(O)25-shRLX2B]
CTC-resin = 2-chlorotrityl resin; TIPS = trisopropylsilane

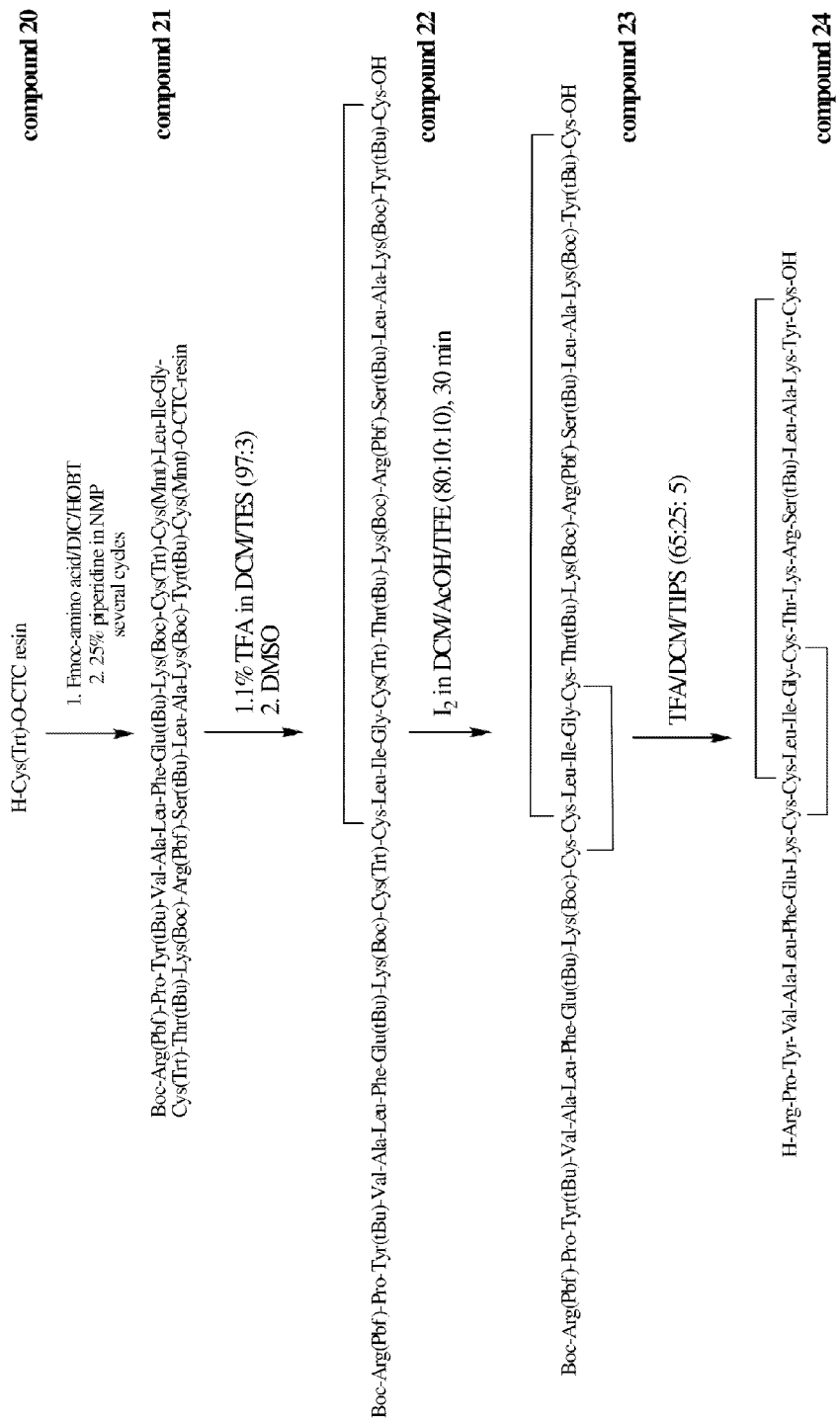
Figure 9. Synthesis of bicyclic RLX1A [compound 24] with the aplication of S-Mmt and Trt protecting groups

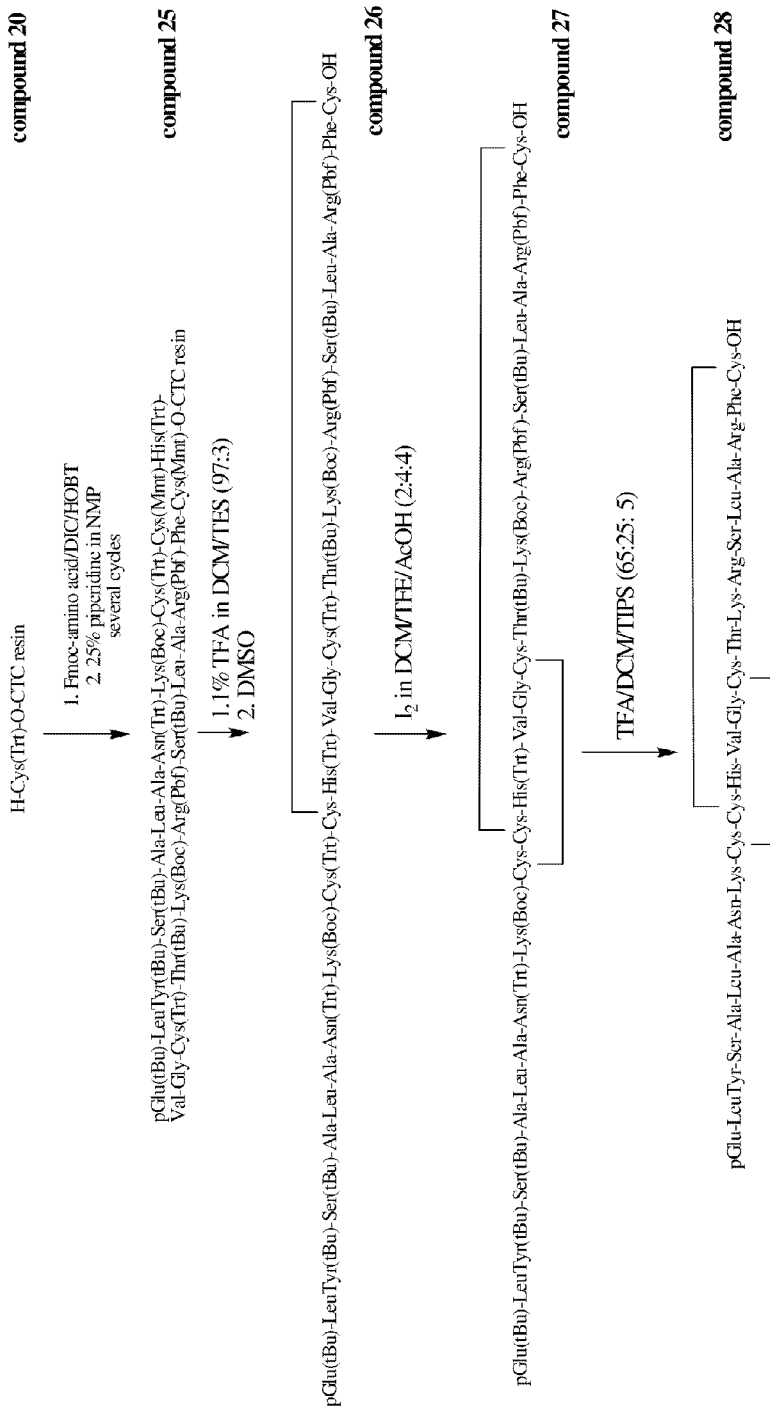
Figure 10. Synthesis of bicyclic human relaxin 2 chain A [compound 28; bicyclic RLX2A] with the aplication of S-Mmt and Trt protecting groups

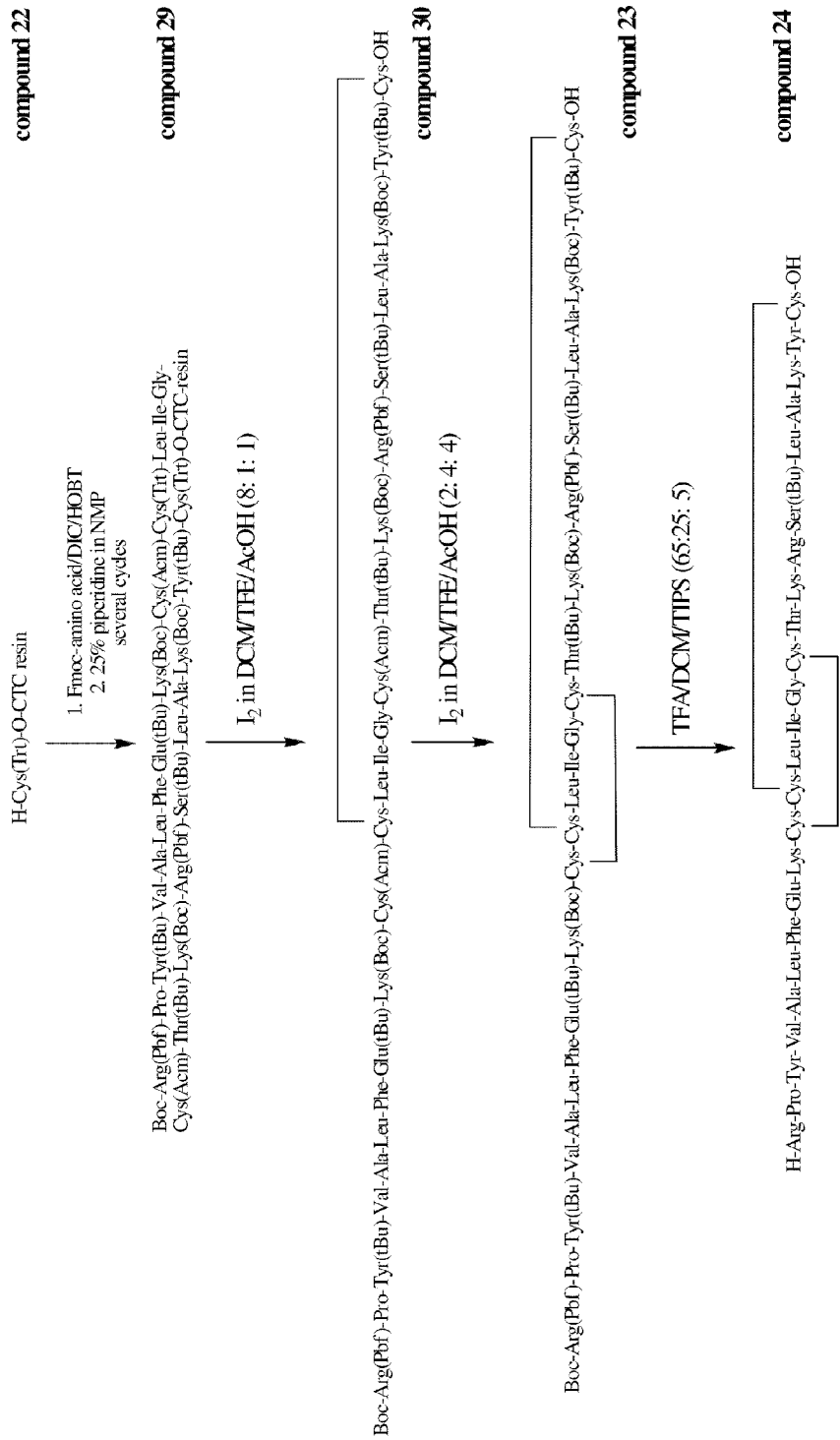
Figure 11. Synthesis of bicyclic human relaxin 1 chain A [RLX1A-chain; compound 24; bicyclic RLX1A] with the aplication of S-Acm and Trt protecting groups

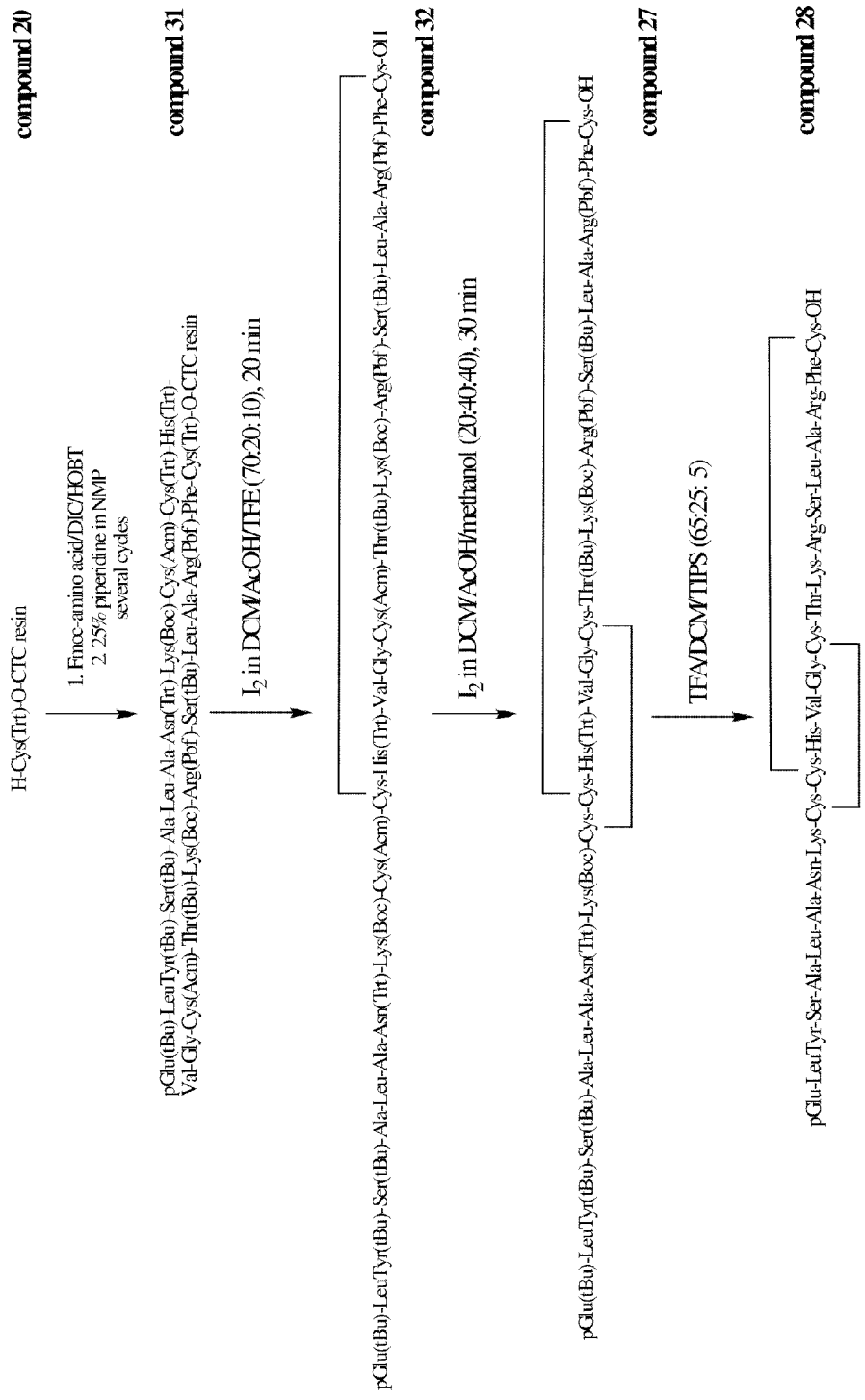
Figure 12. Synthesis of bicyclic human relaxin 2 chain A [compound 19; bicyclic RLX2A] with the aplication of S-Acm and Trt protecting groups

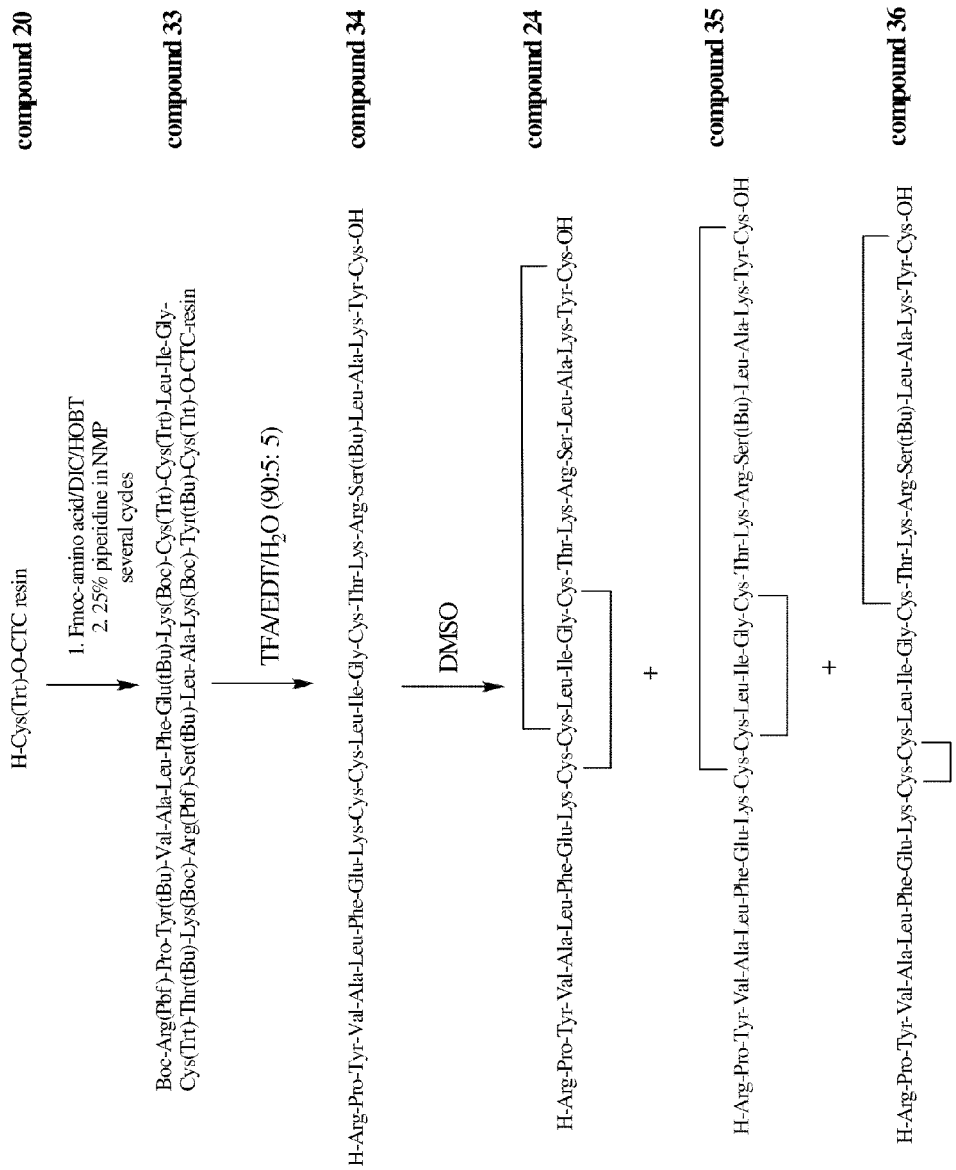
Figure 13. Synthesis of a mixture of bicyclic synthetic human relaxin 1 chains A [compounds 24, 35-36; bicyclic RLX1A] by the DMSO oxidation of the linear chain

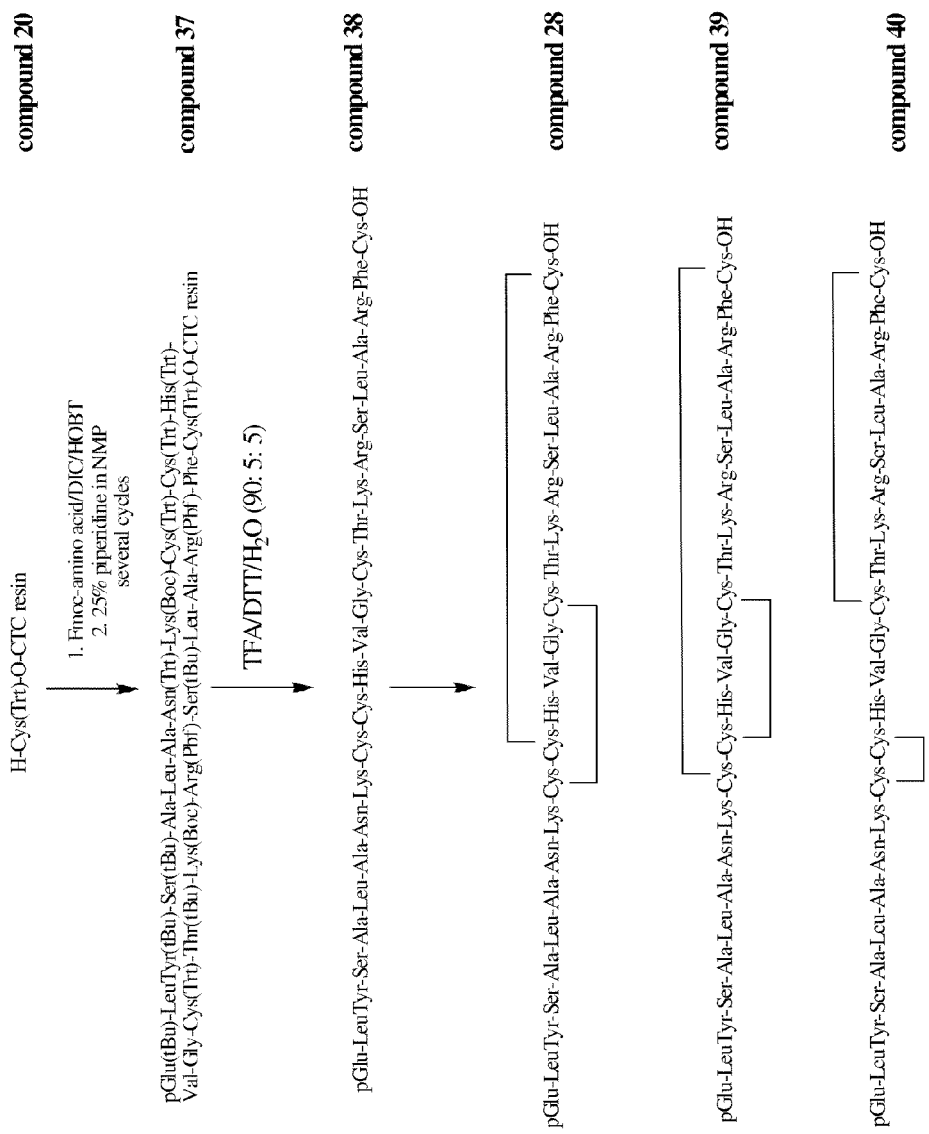
compound 20
compound 37
compound 38
compound 28
compound 39
compound 40
CTC = 2-chlorotrityl resin; TFA = trifluroacetic acid; EDT = dithiothreitol
Figure 14. Synthesis of a mixture of bicyclic synthetic human relaxin 2 chains A [compounds 28, 39-40; bicyclic RLX2A] by the DMSO oxidation of the linear chain

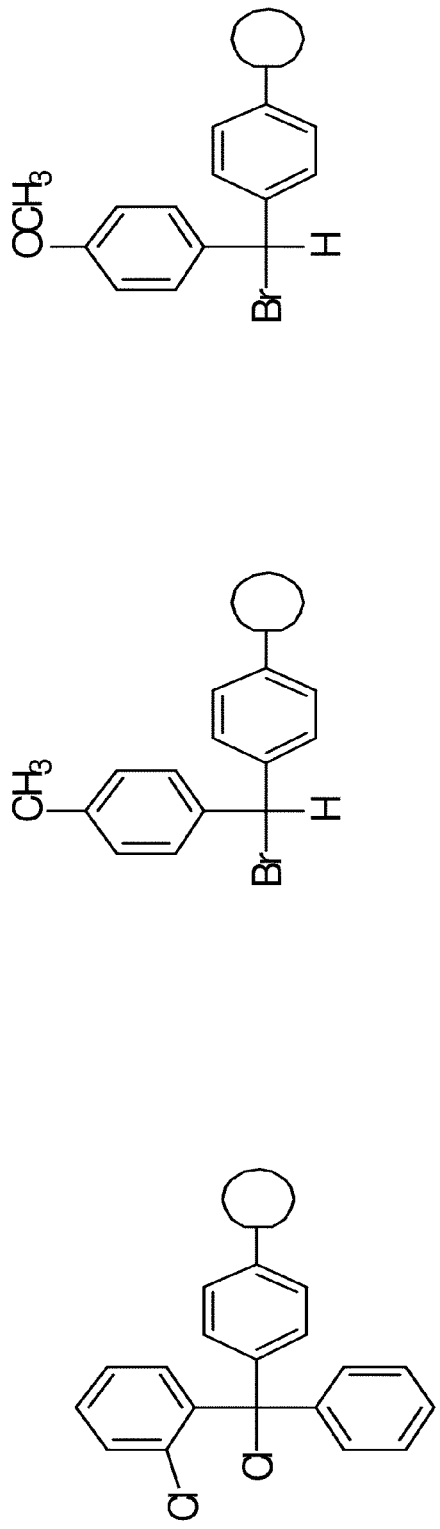
Figure 15. Examples of resins of the trityl and benzhydryl-type used for the synthesis of RLXs A- and B-chains

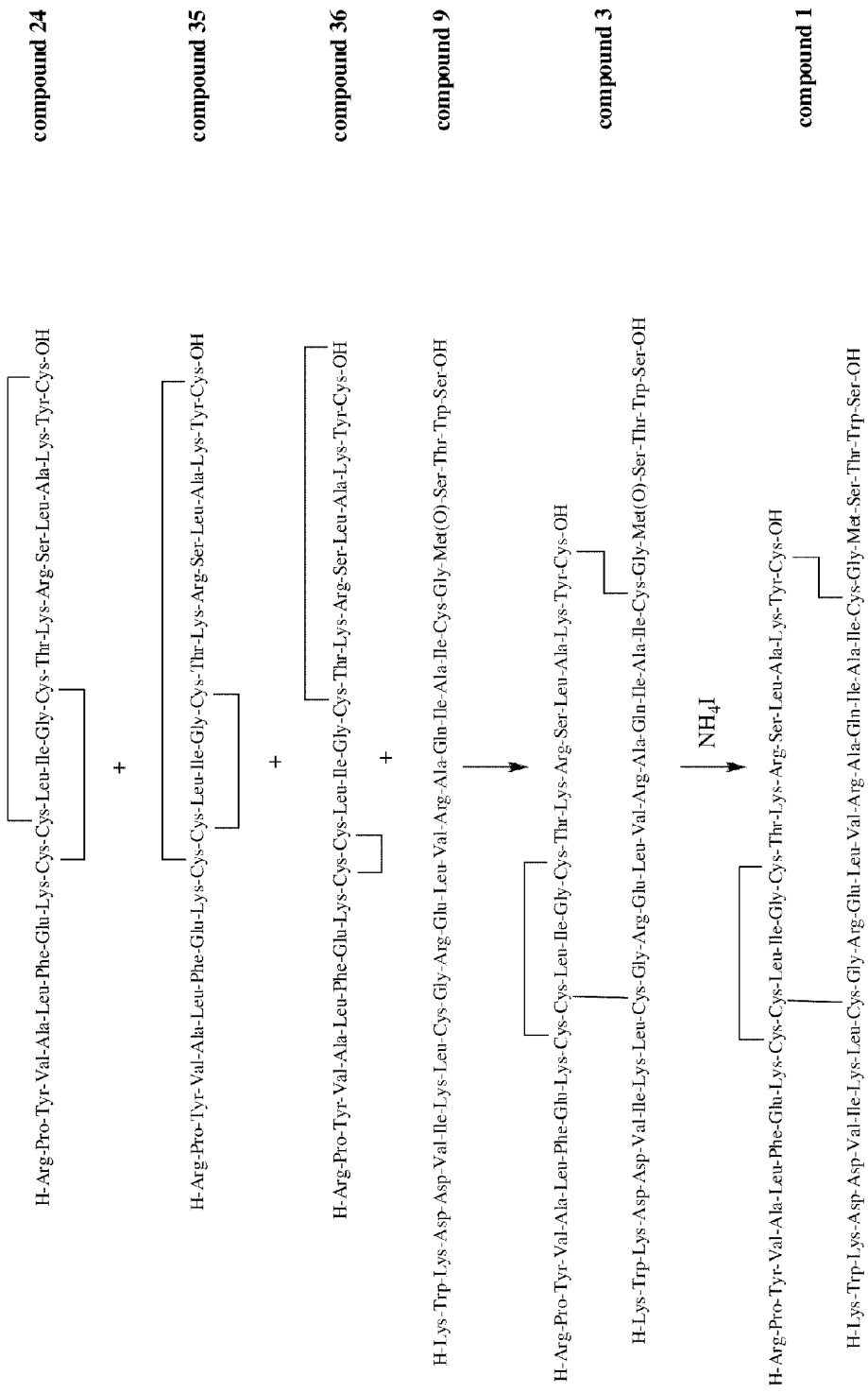
Figure 16. Synthesis of Met(O)$^{24}$-Relaxin 1 [Met(O)$^{24}$-RLX1; compound 3] and of Relaxin 1 [RLX1; compound 1] by chain combination of bicyclic RLX1A and reduced RLX1B-chains

Figure 17. Synthesis of Met(O)$^{24}$-Relaxin 1 [Met(O)$^{24}$-RLX1] and of Relaxin 1 [RLX1] by chain combination of bicyclic RLX1A and cyclic RLX1B-chains

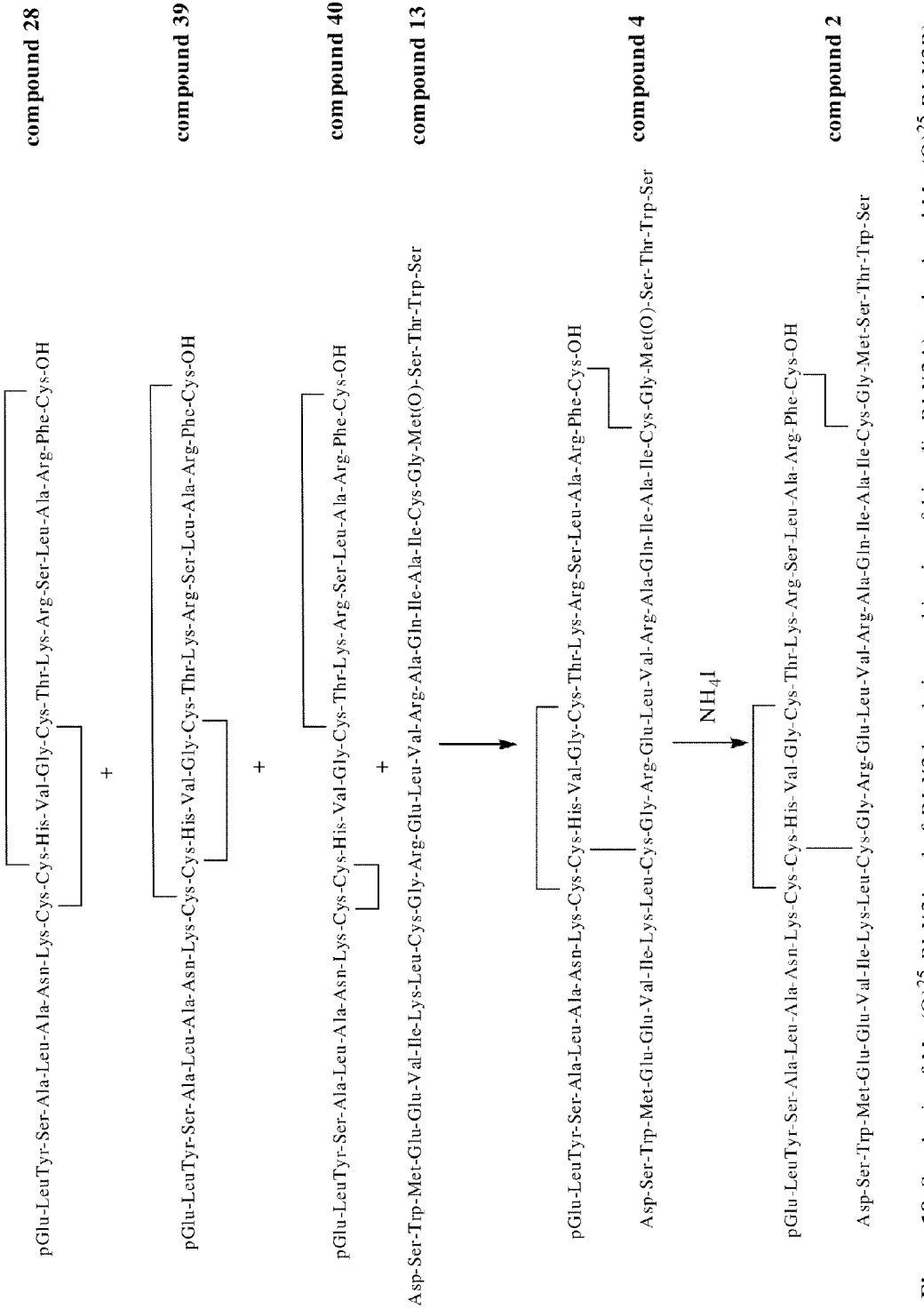
Figure 18. Synthesis of Met(O)$^{25}$-RLX2] and of RLX2 by chain combination of bicyclic RLX2A) and reduced Met(O)$^{25}$-RLX2B)

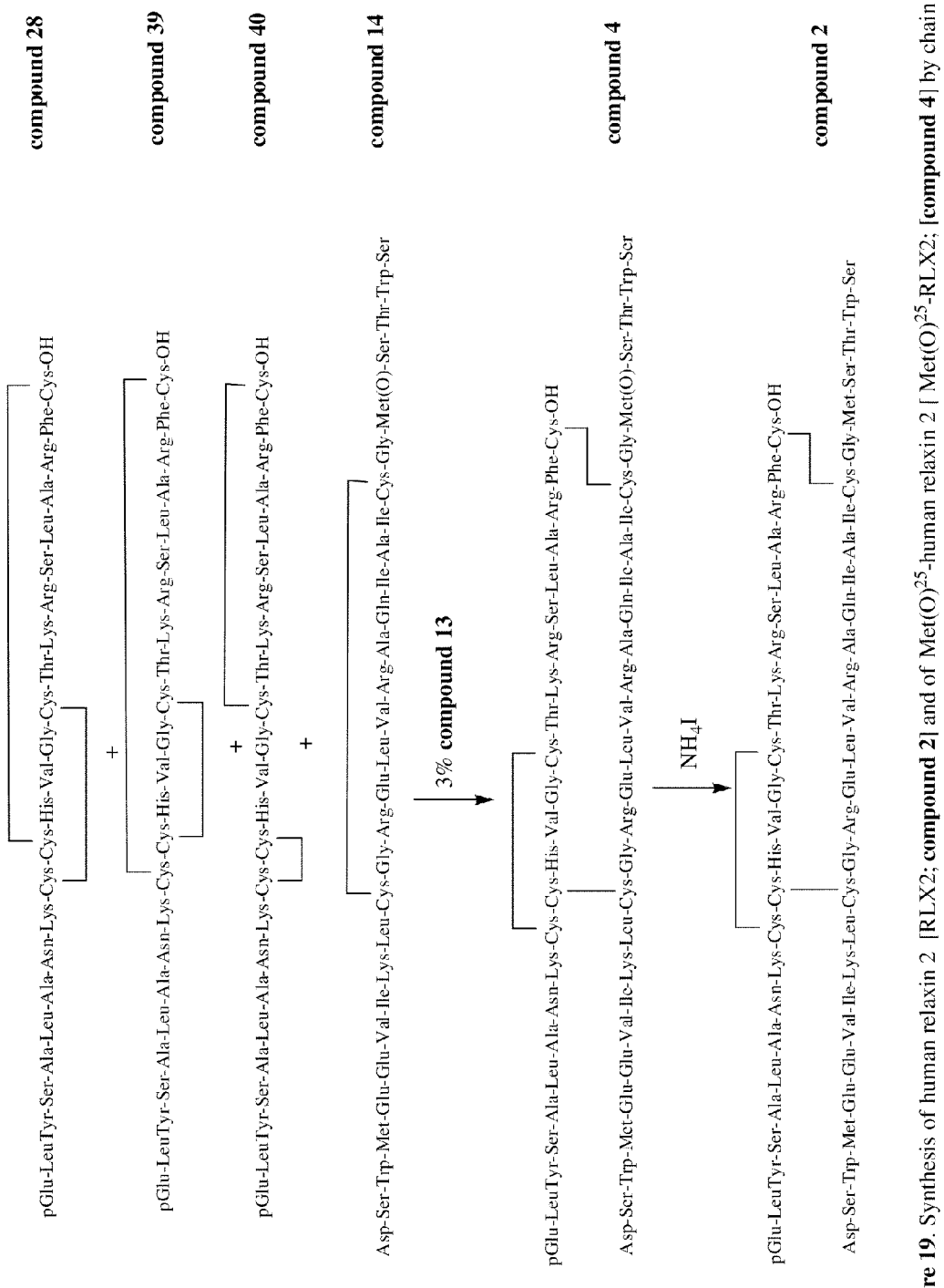
Figure 19. Synthesis of human relaxin 2 [RLX2; compound 2] and of Met(O)$^{25}$-human relaxin 2 [ Met(O)$^{25}$-RLX2; [compound 4] by chain combination of bicyclic RLX2A and cyclic Met(O)$^{25}$-RLX2B)

SEQUENCE LISTING

```
<160> NUMBER OF SEQ ID NOS: 29

<210> SEQ ID NO 1
<211> LENGTH: 6
<212> TYPE: PRT
<213> ORGANISM: Homo sapiens

<400> SEQUENCE: 1

Ala Gln Ile Ala Ile Cys
1               5

<210> SEQ ID NO 2
<211> LENGTH: 24
<212> TYPE: PRT
<213> ORGANISM: Homo sapiens

<400> SEQUENCE: 2
```

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 3
<211> LENGTH: 28
<212> TYPE: PRT
<213> ORGANISM: Homo sapiens

<400> SEQUENCE: 3

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 4
<211> LENGTH: 24
<212> TYPE: PRT
<213> ORGANISM: Homo sapiens

<400> SEQUENCE: 4

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 5
<211> LENGTH: 29
<212> TYPE: PRT
<213> ORGANISM: Homo sapiens

<400> SEQUENCE: 5

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 6
<211> LENGTH: 28
<212> TYPE: PRT
<213> ORGANISM: Homo sapiens
<220> FEATURE:
<221> NAME/KEY: misc
<222> LOCATION: (24)..(24)
<223> OTHER INFORMATION: Met is oxidised.

<400> SEQUENCE: 6

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 7
<211> LENGTH: 29
<212> TYPE: PRT
<213> ORGANISM: Homo sapiens
<220> FEATURE:
<221> NAME/KEY: misc
<222> LOCATION: (25)..(25)
<223> OTHER INFORMATION: Met is oxidised

<400> SEQUENCE: 7

Asp Ser Trp Met Glu Glu Val Ile Lys Leu Cys Gly Arg Glu Leu Val

```
1               5                   10                  15
Arg Ala Gln Ile Ala Ile Cys Gly Met Ser Thr Trp Ser
            20                  25
```

<210> SEQ ID NO 8
<211> LENGTH: 5
<212> TYPE: PRT
<213> ORGANISM: Homo sapiens
<220> FEATURE:
<221> NAME/KEY: misc
<222> LOCATION: (2)..(2)
<223> OTHER INFORMATION: Ser is Ser(tBu) (serine tert-butyl ether)
<220> FEATURE:
<221> NAME/KEY: misc
<222> LOCATION: (3)..(3)
<223> OTHER INFORMATION: Thr is Thr(tBu) (threonine tert-butyl ether)
<220> FEATURE:
<221> NAME/KEY: misc
<222> LOCATION: (4)..(4)
<223> OTHER INFORMATION: Trp is Trp(Boc) (tertbutyloxycarbonyl
      tryptophan)
<220> FEATURE:
<221> NAME/KEY: misc
<222> LOCATION: (5)..(5)
<223> OTHER INFORMATION: Ser is Ser(tBu) (serine tert-butyl ether)

<400> SEQUENCE: 8

```
Met Ser Thr Trp Ser
1               5
```

<210> SEQ ID NO 9
<211> LENGTH: 5
<212> TYPE: PRT
<213> ORGANISM: Homo sapiens
<220> FEATURE:
<221> NAME/KEY: misc
<222> LOCATION: (1)..(1)
<223> OTHER INFORMATION: Met is oxidised to sulfoxide
<220> FEATURE:
<221> NAME/KEY: misc
<222> LOCATION: (2)..(2)
<223> OTHER INFORMATION: Ser is Ser (tBu) (serine tert-butl ether)
<220> FEATURE:
<221> NAME/KEY: misc
<222> LOCATION: (3)..(3)
<223> OTHER INFORMATION: Thr is Thr (tBu) (Threonine tert-butl ether)
<220> FEATURE:
<221> NAME/KEY: misc
<222> LOCATION: (4)..(4)
<223> OTHER INFORMATION: Trp is Trp (Boc) (tertbutyloxycarbonyl
      tryptophan)
<220> FEATURE:
<221> NAME/KEY: misc
<222> LOCATION: (5)..(5)
<223> OTHER INFORMATION: Ser is Ser (tBu) (serine tert-butyl ether)

<400> SEQUENCE: 9

```
Met Ser Thr Trp Ser
1               5
```

<210> SEQ ID NO 10
<211> LENGTH: 28
<212> TYPE: PRT
<213> ORGANISM: Homo sapiens
<220> FEATURE:
<221> NAME/KEY: misc
<222> LOCATION: (1)..(1)
<223> OTHER INFORMATION: Lys is Lys(Boc): tertbutyloxycarbonyl lysine
<220> FEATURE:
<221> NAME/KEY: misc
<222> LOCATION: (3)..(3)
<223> OTHER INFORMATION: Lys is Lys(Boc): tertbutyloxycarbonyl lysine
<220> FEATURE:

```
<221> NAME/KEY: misc
<222> LOCATION: (4)..(5)
<223> OTHER INFORMATION: Asp is Asp(tBu): aspartic acid tert-butyl
      ester
<220> FEATURE:
<221> NAME/KEY: misc
<222> LOCATION: (8)..(8)
<223> OTHER INFORMATION: Lys is Lys(Boc): tertbutyloxycarbonyl lysine
<220> FEATURE:
<221> NAME/KEY: misc
<222> LOCATION: (10)..(10)
<223> OTHER INFORMATION: Cys is Cys(Y): S-trityl cysteine; or S-p-
      methoxytrityl cysteine
<220> FEATURE:
<221> NAME/KEY: misc
<222> LOCATION: (12)..(12)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (13)..(13)
<223> OTHER INFORMATION: Glu is Glu(tBu): glutamic acid tert-butyl
      ester
<220> FEATURE:
<221> NAME/KEY: misc
<222> LOCATION: (16)..(16)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (18)..(18)
<223> OTHER INFORMATION: Gln is Gln(Z): N-benzyloxycarbonyl glutamine;
      or H-glutamine
<220> FEATURE:
<221> NAME/KEY: misc
<222> LOCATION: (22)..(22)
<223> OTHER INFORMATION: Cys is Cys(Y): S-trityl cysteine; or
      S-p-methoxytrityl cysteine
<220> FEATURE:
<221> NAME/KEY: misc
<222> LOCATION: (24)..(24)
<223> OTHER INFORMATION: Met is Met(O): methionine sulfoxide
<220> FEATURE:
<221> NAME/KEY: misc
<222> LOCATION: (25)..(25)
<223> OTHER INFORMATION: Ser is Ser(V): serine tert-butyl ether or
      O-trityl serine
<220> FEATURE:
<221> NAME/KEY: misc
<222> LOCATION: (26)..(26)
<223> OTHER INFORMATION: Thr is Thr(tBu): threonine tert-butyl ether
<220> FEATURE:
<221> NAME/KEY: misc
<222> LOCATION: (27)..(27)
<223> OTHER INFORMATION: Trp is Trp(X): H-tryptophan
<220> FEATURE:
<221> NAME/KEY: misc
<222> LOCATION: (28)..(28)
<223> OTHER INFORMATION: Ser is Ser(V): serine tert-butyl ether or
      O-trtyl serine

<400> SEQUENCE: 10

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 11
<211> LENGTH: 29
<212> TYPE: PRT
<213> ORGANISM: Homo sapiens
<220> FEATURE:
<221> NAME/KEY: misc
<222> LOCATION: (1)..(1)
<223> OTHER INFORMATION: Asp is Asp(tBu): aspartic acid tert-butyl
      ester
```

```
<220> FEATURE:
<221> NAME/KEY: misc
<222> LOCATION: (2)..(2)
<223> OTHER INFORMATION: Ser is Ser(V): serine tert-butyl ether or
      O-trityl serine
<220> FEATURE:
<221> NAME/KEY: misc
<222> LOCATION: (5)..(6)
<223> OTHER INFORMATION: Glu is Glu(tBu): glutamic acid tert-butyl
      ester
<220> FEATURE:
<221> NAME/KEY: misc
<222> LOCATION: (9)..(9)
<223> OTHER INFORMATION: Lys is Lys(Boc): tertbutyloxycarbonyl lysine
<220> FEATURE:
<221> NAME/KEY: misc
<222> LOCATION: (11)..(11)
<223> OTHER INFORMATION: Cys is Cys(Y): S-trityl cysteine; or
      S-p-methoxytrityl cysteine
<220> FEATURE:
<221> NAME/KEY: misc
<222> LOCATION: (13)..(13)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (14)..(14)
<223> OTHER INFORMATION: Glu is Glu(tBu): glutamic acid tert-butyl
      ester
<220> FEATURE:
<221> NAME/KEY: misc
<222> LOCATION: (17)..(17)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Gln is Gln(Z): N-benzyloxycarbonyl glutamine;
      or H-glutamine
<220> FEATURE:
<221> NAME/KEY: misc
<222> LOCATION: (23)..(23)
<223> OTHER INFORMATION: Cys is Cys(Y): S-trityl cysteine; or
      S-p-methoxytrityl cysteine
<220> FEATURE:
<221> NAME/KEY: misc
<222> LOCATION: (25)..(25)
<223> OTHER INFORMATION: Met is Met(O): methionine sulfoxide
<220> FEATURE:
<221> NAME/KEY: misc
<222> LOCATION: (26)..(26)
<223> OTHER INFORMATION: Ser is Ser(V): serine tert-butyl ether or
      O-trityl serine
<220> FEATURE:
<221> NAME/KEY: misc
<222> LOCATION: (27)..(27)
<223> OTHER INFORMATION: Thr is Thr(V): Threonine tert-butyl ether
<220> FEATURE:
<221> NAME/KEY: misc
<222> LOCATION: (29)..(29)
<223> OTHER INFORMATION: Ser is Ser(V): serine tert-butyl etheror
      O-trityl serine

<400> SEQUENCE: 11

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 12
<211> LENGTH: 29
<212> TYPE: PRT
<213> ORGANISM: Homo sapiens
<220> FEATURE:
<221> NAME/KEY: misc
<222> LOCATION: (1)..(1)
```

```
<223> OTHER INFORMATION: Asp is Asp(tBu):  aspartic acid tert-butyl
      ester
<220> FEATURE:
<221> NAME/KEY: misc
<222> LOCATION: (2)..(2)
<223> OTHER INFORMATION: Ser is Ser(tBu):  serine tert-butyl ether
<220> FEATURE:
<221> NAME/KEY: misc
<222> LOCATION: (3)..(3)
<223> OTHER INFORMATION: Trp is Trp(Boc):  tertbutyloxycarbonyl
      tryptophan
<220> FEATURE:
<221> NAME/KEY: misc
<222> LOCATION: (5)..(6)
<223> OTHER INFORMATION: Glu is Glu(tBu):  glutamic acid tert-butyl
      ester
<220> FEATURE:
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (11)..(11)
<223> OTHER INFORMATION: Cys is Cys(Trt):  S-trityl cysteine
<220> FEATURE:
<221> NAME/KEY: misc
<222> LOCATION: (13)..(13)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (14)..(14)
<223> OTHER INFORMATION: Glu is Glu(tBu):  glutamic acid tert-butyl
      ester
<220> FEATURE:
<221> NAME/KEY: misc
<222> LOCATION: (17)..(17)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Gln is Gln(Trt):  N-trityl glutamine
<220> FEATURE:
<221> NAME/KEY: misc
<222> LOCATION: (23)..(23)
<223> OTHER INFORMATION: Cys is Cys(Trt):  S-trityl cysteine
<220> FEATURE:
<221> NAME/KEY: misc
<222> LOCATION: (25)..(25)
<223> OTHER INFORMATION: Met is Met(O):  methionine sulfoxide
<220> FEATURE:
<221> NAME/KEY: misc
<222> LOCATION: (26)..(26)
<223> OTHER INFORMATION: Ser is Ser(tBu):  serine tert-butyl ether
<220> FEATURE:
<221> NAME/KEY: misc
<222> LOCATION: (27)..(27)
<223> OTHER INFORMATION: Thr is Thr(tBu):  Threonine tert-butyl ether
<220> FEATURE:
<221> NAME/KEY: misc
<222> LOCATION: (29)..(29)
<223> OTHER INFORMATION: Ser is Ser(tBu):  serine tert-butyl ether

<400> SEQUENCE: 12

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 13
<211> LENGTH: 28
<212> TYPE: PRT
<213> ORGANISM: Homo sapiens
<220> FEATURE:
<221> NAME/KEY: misc
```

```
<222> LOCATION: (1)..(1)
<223> OTHER INFORMATION: Lys is Lys(Boc):  tertbutyloxycarbonyl lysine
<220> FEATURE:
<221> NAME/KEY: misc
<222> LOCATION: (3)..(3)
<223> OTHER INFORMATION: Lys is Lys(Boc):  tertbutyloxycarbonyl lysine
<220> FEATURE:
<221> NAME/KEY: misc
<222> LOCATION: (4)..(5)
<223> OTHER INFORMATION: Asp is  Asp(tBu):  aspartic acid tert-butyl
      ester
<220> FEATURE:
<221> NAME/KEY: misc
<222> LOCATION: (8)..(8)
<223> OTHER INFORMATION: Lys is Lys(Boc):  tertbutyloxycarbonyl lysine
<220> FEATURE:
<221> NAME/KEY: misc
<222> LOCATION: (12)..(12)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (13)..(13)
<223> OTHER INFORMATION: Glu is Glu(tBu):  glutamic acid tert-butyl
      ester
<220> FEATURE:
<221> NAME/KEY: misc
<222> LOCATION: (16)..(16)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (18)..(18)
<223> OTHER INFORMATION: Gln is Gln(Trt):  N-S-trityl glutamine
<220> FEATURE:
<221> NAME/KEY: misc
<222> LOCATION: (24)..(24)
<223> OTHER INFORMATION: Met is Met(O):  methionine sulfoxide
<220> FEATURE:
<221> NAME/KEY: misc
<222> LOCATION: (25)..(25)
<223> OTHER INFORMATION: Ser is Ser(tBu):  serine tert-butyl ether
<220> FEATURE:
<221> NAME/KEY: misc
<222> LOCATION: (26)..(26)
<223> OTHER INFORMATION: Thr is Thr(tBu):  threonine tert-butyl ether
<220> FEATURE:
<221> NAME/KEY: misc
<222> LOCATION: (27)..(27)
<223> OTHER INFORMATION: Trp is Trp(Boc):  tertbutyloxycarbonyl
      tryptophan
<220> FEATURE:
<221> NAME/KEY: misc
<222> LOCATION: (28)..(28)
<223> OTHER INFORMATION: Ser is Ser(tBu):  serine tert-butyl ether

<400> SEQUENCE: 13

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 14
<211> LENGTH: 29
<212> TYPE: PRT
<213> ORGANISM: Homo sapiens
<220> FEATURE:
<221> NAME/KEY: misc
<222> LOCATION: (1)..(1)
<223> OTHER INFORMATION: Asp is Asp(tBu):  aspartic acid tert-butyl
      ester
<220> FEATURE:
<221> NAME/KEY: misc
<222> LOCATION: (2)..(2)
<223> OTHER INFORMATION: Ser is Ser(tBu):  serine tert-butyl ether
<220> FEATURE:
```

```
<221> NAME/KEY: misc
<222> LOCATION: (3)..(3)
<223> OTHER INFORMATION: Trp is Trp(Boc): tertbutyloxycarbonyl
      tryptophan
<220> FEATURE:
<221> NAME/KEY: misc
<222> LOCATION: (5)..(6)
<223> OTHER INFORMATION: Glu is Glu(tBu): glutamic acid tert-butyl
      ester
<220> FEATURE:
<221> NAME/KEY: misc
<222> LOCATION: (9)..(9)
<223> OTHER INFORMATION: Lys is Lys(Boc): tertbutyloxycarbonyl lysine
<220> FEATURE:
<221> NAME/KEY: misc
<222> LOCATION: (13)..(13)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (14)..(14)
<223> OTHER INFORMATION: Glu is Glu(tBu): glutamic acid tert-butyl
      ester
<220> FEATURE:
<221> NAME/KEY: misc
<222> LOCATION: (17)..(17)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Gln is Gln(Trt): N-trityl glutamine
<220> FEATURE:
<221> NAME/KEY: misc
<222> LOCATION: (25)..(25)
<223> OTHER INFORMATION: Met is Met(O): methionine sulfoxide
<220> FEATURE:
<221> NAME/KEY: misc
<222> LOCATION: (26)..(26)
<223> OTHER INFORMATION: Ser is Ser(v): serine tert-butyl ether
<220> FEATURE:
<221> NAME/KEY: misc
<222> LOCATION: (27)..(27)
<223> OTHER INFORMATION: Thr is Thr(tBu): Threonine tert-butyl ether
<220> FEATURE:
<221> NAME/KEY: misc
<222> LOCATION: (28)..(28)
<223> OTHER INFORMATION: Trp is Trp(Boc): tertbutyloxycarbonyl
      tryptophan
<220> FEATURE:
<221> NAME/KEY: misc
<222> LOCATION: (29)..(29)
<223> OTHER INFORMATION: Ser is Ser(tBu): serine tert-butyl ether

<400> SEQUENCE: 14

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 15
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (3)..(3)
<223> OTHER INFORMATION: Tyr is Tyr(tBu): tyrosine tert-butyl ether
<220> FEATURE:
<221> NAME/KEY: misc
<222> LOCATION: (8)..(8)
```

```
<223> OTHER INFORMATION: Glu is Glu(tBu):  glutamic acid tert-butyl
      ester
<220> FEATURE:
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is Cys(Trt):  S-trityl cysteine
<220> FEATURE:
<221> NAME/KEY: misc
<222> LOCATION: (11)..(11)
<223> OTHER INFORMATION: Cys is Cys(Mmt):  Mmt:  Monomethoxytrityl
      cysteine
<220> FEATURE:
<221> NAME/KEY: misc
<222> LOCATION: (15)..(15)
<223> OTHER INFORMATION: Cys is Cys(Trt):  S-trityl cysteine
<220> FEATURE:
<221> NAME/KEY: misc
<222> LOCATION: (16)..(16)
<223> OTHER INFORMATION: Thr is Thr(tBu):  threonine tert-butyl ether
<220> FEATURE:
<221> NAME/KEY: misc
<222> LOCATION: (17)..(17)
<223> OTHER INFORMATION: Lys is Lys(Boc):  tertbutyloxycarbonyl lysine
<220> FEATURE:
<221> NAME/KEY: misc
<222> LOCATION: (18)..(18)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu):  serine tert-butyl ether
<220> FEATURE:
<221> NAME/KEY: misc
<222> LOCATION: (22)..(22)
<223> OTHER INFORMATION: Lys is Lys(Boc):  tertbutyloxycarbonyl lysine
<220> FEATURE:
<221> NAME/KEY: misc
<222> LOCATION: (23)..(23)
<223> OTHER INFORMATION: Tyr is Tyr(tBu):  tyrosine tert-butyl ether
<220> FEATURE:
<221> NAME/KEY: misc
<222> LOCATION: (24)..(24)
<223> OTHER INFORMATION: Cys is Cys(Mmt):  Mmt:  Monomethoxytrityl
      cysteine

<400> SEQUENCE: 15

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 16
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (3)..(3)
<223> OTHER INFORMATION: Tyr is Tyr(tBu):  tyrosine tert-butyl ether
<220> FEATURE:
<221> NAME/KEY: misc
<222> LOCATION: (8)..(8)
<223> OTHER INFORMATION: Glu is Glu(tBu):  glutamic acid tert-butyl
      ester
<220> FEATURE:
<221> NAME/KEY: misc
```

<222> LOCATION: (9)..(9)
<223> OTHER INFORMATION: Lys is Lys(Boc): tertbutyloxycarbonyl lysine
<220> FEATURE:
<221> NAME/KEY: misc
<222> LOCATION: (10)..(10)
<223> OTHER INFORMATION: Cys is Cys(Trt): S-trityl cysteine
<220> FEATURE:
<221> NAME/KEY: misc
<222> LOCATION: (11)..(11)
<223> OTHER INFORMATION: Cys is connected to Cys at position 24
<220> FEATURE:
<221> NAME/KEY: misc
<222> LOCATION: (15)..(15)
<223> OTHER INFORMATION: Cys is Cys(Trt): S-trityl cysteine
<220> FEATURE:
<221> NAME/KEY: misc
<222> LOCATION: (16)..(16)
<223> OTHER INFORMATION: Thr is Thr(tBu): threonine tert-butyl ether
<220> FEATURE:
<221> NAME/KEY: misc
<222> LOCATION: (17)..(17)
<223> OTHER INFORMATION: Lys is Lys(Boc): tertbutyloxycarbonyl lysine
<220> FEATURE:
<221> NAME/KEY: misc
<222> LOCATION: (18)..(18)
<223> OTHER INFORMATION: Arg is Arg(Pbf):
    2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu): serine tert-butyl ether
<220> FEATURE:
<221> NAME/KEY: misc
<222> LOCATION: (22)..(22)
<223> OTHER INFORMATION: Lys is Lys(Boc): tertbutyloxycarbonyl lysine
<220> FEATURE:
<221> NAME/KEY: misc
<222> LOCATION: (23)..(23)
<223> OTHER INFORMATION: Tyr is Tyr(tBu): tyrosine tert-butyl ether
<220> FEATURE:
<221> NAME/KEY: misc
<222> LOCATION: (24)..(24)
<223> OTHER INFORMATION: Cys is connected with Cys at position 11

<400> SEQUENCE: 16

Arg Pro Tyr Val Ala Leu Phe Glu Lys Cys Cys Leu Ile Gly Cys Thr
1               5                  10                  15

Lys Arg Ser Leu Ala Lys Tyr Cys
            20

<210> SEQ ID NO 17
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Arg is Arg(Pbf):
    2,2,4,6,7-pentamethyldihydrobenzofuran-5-sulfonyl arginine
<220> FEATURE:
<221> NAME/KEY: misc
<222> LOCATION: (3)..(3)
<223> OTHER INFORMATION: Tyr is Tyr(tBu): tyrosine tert-butyl ether
<220> FEATURE:
<221> NAME/KEY: misc
<222> LOCATION: (8)..(8)
<223> OTHER INFORMATION: Glu is Glu(tBu): glutamic acid tert-butyl
    ester
<220> FEATURE:
<221> NAME/KEY: misc
<222> LOCATION: (9)..(9)
<223> OTHER INFORMATION: Lys is Lys(Boc): tertbutyloxycarbonyl lysine
<220> FEATURE:
<221> NAME/KEY: misc
<222> LOCATION: (10)..(10)
<223> OTHER INFORMATION: Cys is connected to Cys at position 15

```
<220> FEATURE:
<221> NAME/KEY: misc
<222> LOCATION: (11)..(11)
<223> OTHER INFORMATION: Cys is connected to Cys at position 24
<220> FEATURE:
<221> NAME/KEY: misc
<222> LOCATION: (15)..(15)
<223> OTHER INFORMATION: Cys is connected to Cys at position 10
<220> FEATURE:
<221> NAME/KEY: misc
<222> LOCATION: (16)..(16)
<223> OTHER INFORMATION: Thr is Thr(tBu): threonine tert-butyl ether
<220> FEATURE:
<221> NAME/KEY: misc
<222> LOCATION: (17)..(17)
<223> OTHER INFORMATION: Lys is Lys(Boc): tertbutyloxycarbonyl lysine
<220> FEATURE:
<221> NAME/KEY: misc
<222> LOCATION: (18)..(18)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu): serine tert-butyl ether
<220> FEATURE:
<221> NAME/KEY: misc
<222> LOCATION: (22)..(22)
<223> OTHER INFORMATION: Lys is Lys(Boc): tertbutyloxycarbonyl lysine
<220> FEATURE:
<221> NAME/KEY: misc
<222> LOCATION: (23)..(23)
<223> OTHER INFORMATION: Tyr is Tyr(tBu): tyrosine tert-butyl ether
<220> FEATURE:
<221> NAME/KEY: misc
<222> LOCATION: (24)..(24)
<223> OTHER INFORMATION: Cys is connected to Cys at position 11

<400> SEQUENCE: 17

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 18
<211> LENGTH: 24
<212> TYPE: PRT
<213> ORGANISM: Homo sapiens

<400> SEQUENCE: 18

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 19
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Glu is Glu(tBu): glutamic acid tert-butyl
      ester
<220> FEATURE:
<221> NAME/KEY: misc
<222> LOCATION: (3)..(3)
<223> OTHER INFORMATION: Tyr is Tyr(tBu): tyrosine tert-butyl ester
<220> FEATURE:
<221> NAME/KEY: misc
<222> LOCATION: (4)..(4)
<223> OTHER INFORMATION: Ser is Ser(tBu): serine tert-butyl ether
<220> FEATURE:
```

```
<221> NAME/KEY: misc
<222> LOCATION: (8)..(8)
<223> OTHER INFORMATION: Asn is Asn(tBu): Asparagine tert-butyl ester
<220> FEATURE:
<221> NAME/KEY: misc
<222> LOCATION: (9)..(9)
<223> OTHER INFORMATION: Lys is Lys(Boc): tertbutyloxycarbonyl lysine
<220> FEATURE:
<221> NAME/KEY: misc
<222> LOCATION: (10)..(10)
<223> OTHER INFORMATION: Cys is Cys(Y): S-trityl cysteine
<220> FEATURE:
<221> NAME/KEY: misc
<222> LOCATION: (11)..(11)
<223> OTHER INFORMATION: Cys is Cys(Mmt): Monomethoxytrityl cysteine
<220> FEATURE:
<221> NAME/KEY: misc
<222> LOCATION: (12)..(12)
<223> OTHER INFORMATION: His is His(Trt): S-trityl histitine
<220> FEATURE:
<221> NAME/KEY: misc
<222> LOCATION: (15)..(15)
<223> OTHER INFORMATION: Cys is Cys(Trt): S-trityl Cystetine
<220> FEATURE:
<221> NAME/KEY: misc
<222> LOCATION: (16)..(16)
<223> OTHER INFORMATION: Thr is Thr(tBu): threonine tert-butyl ether
<220> FEATURE:
<221> NAME/KEY: misc
<222> LOCATION: (17)..(17)
<223> OTHER INFORMATION: Lys is Lys(Boc): tertbutyloxycarbonyl lysine
<220> FEATURE:
<221> NAME/KEY: misc
<222> LOCATION: (18)..(18)
<223> OTHER INFORMATION: Arg is Arg(Pbf):
     2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu): serine tert-butyl ether
<220> FEATURE:
<221> NAME/KEY: misc
<222> LOCATION: (22)..(22)
<223> OTHER INFORMATION: Arg is Arg(Pbf):
     2,2,4,6,7-pentamethyldihydrobenzofuran-5-sulfonyl arginine
<220> FEATURE:
<221> NAME/KEY: misc
<222> LOCATION: (24)..(24)
<223> OTHER INFORMATION: Cys is Cys(Mmt): Monomethoxytrityl cystine

<400> SEQUENCE: 19

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 20
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Glu is Glu(tBu): glutamic acid tert-butyl
     ester
<220> FEATURE:
<221> NAME/KEY: misc
<222> LOCATION: (3)..(3)
<223> OTHER INFORMATION: Tyr is Tyr(tBu): tyrosine tert-butyl ester
<220> FEATURE:
<221> NAME/KEY: misc
<222> LOCATION: (4)..(4)
<223> OTHER INFORMATION: Ser is Ser(tBu): serine tert-butyl ether
<220> FEATURE:
<221> NAME/KEY: misc
<222> LOCATION: (8)..(8)
```

```
<223> OTHER INFORMATION: Asn is Asn(tBu):  Asparagine tert-butyl ester
<220> FEATURE:
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is  Cys(Y):  S-trityl cysteine
<220> FEATURE:
<221> NAME/KEY: misc
<222> LOCATION: (11)..(11)
<223> OTHER INFORMATION: Cys is  connected to Cys at position 24
<220> FEATURE:
<221> NAME/KEY: misc
<222> LOCATION: (12)..(12)
<223> OTHER INFORMATION: His is  His(Trt):  S-trityl histitine
<220> FEATURE:
<221> NAME/KEY: misc
<222> LOCATION: (15)..(15)
<223> OTHER INFORMATION: Cys is Cys(Trt):  S-trityl Cystetine
<220> FEATURE:
<221> NAME/KEY: misc
<222> LOCATION: (16)..(16)
<223> OTHER INFORMATION: Thr is Thr(tBu):  threonine tert-butyl ether
<220> FEATURE:
<221> NAME/KEY: misc
<222> LOCATION: (17)..(17)
<223> OTHER INFORMATION: Lys is Lys(Boc):  tertbutyloxycarbonyl lysine
<220> FEATURE:
<221> NAME/KEY: misc
<222> LOCATION: (18)..(18)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu):  serine tert-butyl ether
<220> FEATURE:
<221> NAME/KEY: misc
<222> LOCATION: (22)..(22)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (24)..(24)
<223> OTHER INFORMATION: Cys is connected to Cys at position 11

<400> SEQUENCE: 20

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 21
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Glu is Glu(tBu):  glutamic acid tert-butyl
      ester
<220> FEATURE:
<221> NAME/KEY: misc
<222> LOCATION: (3)..(3)
<223> OTHER INFORMATION: Tyr is Tyr(tBu):  tyrosine tert-butyl ester
<220> FEATURE:
<221> NAME/KEY: misc
<222> LOCATION: (4)..(4)
<223> OTHER INFORMATION: Ser is Ser(tBu):  serine tert-butyl ether
<220> FEATURE:
<221> NAME/KEY: misc
<222> LOCATION: (8)..(8)
<223> OTHER INFORMATION: Asn is Asn(tBu):  Asparagine tert-butyl ester
<220> FEATURE:
```

```
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is  connected to Cys at position 15
<220> FEATURE:
<221> NAME/KEY: misc
<222> LOCATION: (11)..(11)
<223> OTHER INFORMATION: Cys is  connected to Cys at position 24
<220> FEATURE:
<221> NAME/KEY: misc
<222> LOCATION: (12)..(12)
<223> OTHER INFORMATION: His is  His(Trt):  S-trityl histitine
<220> FEATURE:
<221> NAME/KEY: misc
<222> LOCATION: (15)..(15)
<223> OTHER INFORMATION: Cys is connected to Cys at position 11
<220> FEATURE:
<221> NAME/KEY: misc
<222> LOCATION: (16)..(16)
<223> OTHER INFORMATION: Thr is Thr(tBu):  threonine tert-butyl ether
<220> FEATURE:
<221> NAME/KEY: misc
<222> LOCATION: (17)..(17)
<223> OTHER INFORMATION: Lys is Lys(Boc):  tertbutyloxycarbonyl lysine
<220> FEATURE:
<221> NAME/KEY: misc
<222> LOCATION: (18)..(18)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu):  serine tert-butyl ether
<220> FEATURE:
<221> NAME/KEY: misc
<222> LOCATION: (22)..(22)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (24)..(24)
<223> OTHER INFORMATION: Cys is connected to Cys at position 11

<400> SEQUENCE: 21

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 22
<211> LENGTH: 24
<212> TYPE: PRT
<213> ORGANISM: Homo sapiens

<400> SEQUENCE: 22

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 23
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Arg is Arg(Pbf):
      2,2,4,6,7-pentamethyldihydrobenzofuran-5-sulfonyl arginine
<220> FEATURE:
```

```
<221> NAME/KEY: misc
<222> LOCATION: (3)..(3)
<223> OTHER INFORMATION: Tyr is Tyr(tBu):  tyrosine tert-butyl ether
<220> FEATURE:
<221> NAME/KEY: misc
<222> LOCATION: (8)..(8)
<223> OTHER INFORMATION: Glu is Glu(tBu):  glutamic acid tert-butyl
      ester
<220> FEATURE:
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is Cys(Acm):  Acetamidomethyl cysteine
<220> FEATURE:
<221> NAME/KEY: misc
<222> LOCATION: (11)..(11)
<223> OTHER INFORMATION: Cys is Cys(Trt): S-trityl cysteine
<220> FEATURE:
<221> NAME/KEY: misc
<222> LOCATION: (15)..(15)
<223> OTHER INFORMATION: Cys is Cys(Acm):  Acetamidomethyl cysteine
<220> FEATURE:
<221> NAME/KEY: misc
<222> LOCATION: (16)..(16)
<223> OTHER INFORMATION: Thr is Thr(tBu):  threonine tert-butyl ether
<220> FEATURE:
<221> NAME/KEY: misc
<222> LOCATION: (17)..(17)
<223> OTHER INFORMATION: Lys is Lys(Boc):  tertbutyloxycarbonyl lysine
<220> FEATURE:
<221> NAME/KEY: misc
<222> LOCATION: (18)..(18)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu):  serine tert-butyl ether
<220> FEATURE:
<221> NAME/KEY: misc
<222> LOCATION: (22)..(22)
<223> OTHER INFORMATION: Lys is Lys(Boc):  tertbutyloxycarbonyl lysine
<220> FEATURE:
<221> NAME/KEY: misc
<222> LOCATION: (23)..(23)
<223> OTHER INFORMATION: Tyr is Tyr(tBu):  tyrosine tert-butyl ether
<220> FEATURE:
<221> NAME/KEY: misc
<222> LOCATION: (24)..(24)
<223> OTHER INFORMATION: Cys is Cys(Trt): S-trityl cysteine

<400> SEQUENCE: 23

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 24
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (3)..(3)
<223> OTHER INFORMATION: Tyr is Tyr(tBu):  tyrosine tert-butyl ether
<220> FEATURE:
<221> NAME/KEY: misc
<222> LOCATION: (8)..(8)
```

```
<223> OTHER INFORMATION: Glu is Glu(tBu):  glutamic acid tert-butyl
      ester
<220> FEATURE:
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is Cys(Acm):  Acetamidomethyl cysteine
<220> FEATURE:
<221> NAME/KEY: misc
<222> LOCATION: (11)..(11)
<223> OTHER INFORMATION: Cys is connected to Cys at position 24
<220> FEATURE:
<221> NAME/KEY: misc
<222> LOCATION: (15)..(15)
<223> OTHER INFORMATION: Cys is Cys(Acm):  Acetamidomethyl cysteine
<220> FEATURE:
<221> NAME/KEY: misc
<222> LOCATION: (16)..(16)
<223> OTHER INFORMATION: Thr is Thr(tBu):  threonine tert-butyl ether
<220> FEATURE:
<221> NAME/KEY: misc
<222> LOCATION: (17)..(17)
<223> OTHER INFORMATION: Lys is Lys(Boc):  tertbutyloxycarbonyl lysine
<220> FEATURE:
<221> NAME/KEY: misc
<222> LOCATION: (18)..(18)
<223> OTHER INFORMATION: Arg is Arg(Pbf):
      2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu):  serine tert-butyl ether
<220> FEATURE:
<221> NAME/KEY: misc
<222> LOCATION: (22)..(22)
<223> OTHER INFORMATION: Lys is Lys(Boc):  tertbutyloxycarbonyl lysine
<220> FEATURE:
<221> NAME/KEY: misc
<222> LOCATION: (23)..(23)
<223> OTHER INFORMATION: Tyr is Tyr(tBu):  tyrosine tert-butyl ether
<220> FEATURE:
<221> NAME/KEY: misc
<222> LOCATION: (24)..(24)
<223> OTHER INFORMATION: Cys is connected to Cys at position 11

<400> SEQUENCE: 24

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 25
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Glu is Glu(tBu):  glutamic acid tert-butyl
      ester
<220> FEATURE:
<221> NAME/KEY: misc
<222> LOCATION: (3)..(3)
<223> OTHER INFORMATION: Tyr is Tyr(tBu):  tyrosine tert-butyl ester
<220> FEATURE:
<221> NAME/KEY: misc
<222> LOCATION: (4)..(4)
<223> OTHER INFORMATION: Ser is Ser(tBu):  serine tert-butyl ether
<220> FEATURE:
<221> NAME/KEY: misc
<222> LOCATION: (8)..(8)
<223> OTHER INFORMATION: Asn is Asn(tBu):  Asparagine tert-butyl ester
<220> FEATURE:
```

```
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is  Cys(Acm):  Acetamidomethyl cysteine
<220> FEATURE:
<221> NAME/KEY: misc
<222> LOCATION: (11)..(11)
<223> OTHER INFORMATION: Cys is  Cys(Trt):  S-trityl cysteine
<220> FEATURE:
<221> NAME/KEY: misc
<222> LOCATION: (12)..(12)
<223> OTHER INFORMATION: His is  His(Trt):  S-trityl histitine
<220> FEATURE:
<221> NAME/KEY: misc
<222> LOCATION: (15)..(15)
<223> OTHER INFORMATION: Cys is Cys(Acm):  Acetamidomethyl Cystetine
<220> FEATURE:
<221> NAME/KEY: misc
<222> LOCATION: (16)..(16)
<223> OTHER INFORMATION: Thr is Thr(tBu):  threonine tert-butyl ether
<220> FEATURE:
<221> NAME/KEY: misc
<222> LOCATION: (17)..(17)
<223> OTHER INFORMATION: Lys is Lys(Boc):  tertbutyloxycarbonyl lysine
<220> FEATURE:
<221> NAME/KEY: misc
<222> LOCATION: (18)..(18)
<223> OTHER INFORMATION: Arg is Arg(Pbf):
     2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu):  serine tert-butyl ether
<220> FEATURE:
<221> NAME/KEY: misc
<222> LOCATION: (22)..(22)
<223> OTHER INFORMATION: Arg is Arg(Pbf):
     2,2,4,6,7-pentamethyldihydrobenzofuran-5-sulfonyl arginine
<220> FEATURE:
<221> NAME/KEY: misc
<222> LOCATION: (24)..(24)
<223> OTHER INFORMATION: Cys is Cys(Trt): S-trityl cysteine

<400> SEQUENCE: 25

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 26
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Glu is Glu(tBu):  glutamic acid tert-butyl
     ester
<220> FEATURE:
<221> NAME/KEY: misc
<222> LOCATION: (3)..(3)
<223> OTHER INFORMATION: Tyr is Tyr(tBu):  tyrosine tert-butyl ester
<220> FEATURE:
<221> NAME/KEY: misc
<222> LOCATION: (4)..(4)
<223> OTHER INFORMATION: Ser is Ser(tBu):  serine tert-butyl ether
<220> FEATURE:
<221> NAME/KEY: misc
<222> LOCATION: (8)..(8)
<223> OTHER INFORMATION: Asn is Asn(Trt): trityl Asparagine
<220> FEATURE:
<221> NAME/KEY: misc
<222> LOCATION: (9)..(9)
```

```
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is  Cys(Acm):  Acetamidomethyl cysteine
<220> FEATURE:
<221> NAME/KEY: misc
<222> LOCATION: (11)..(11)
<223> OTHER INFORMATION: Cys is  connected to Cys at position 24
<220> FEATURE:
<221> NAME/KEY: misc
<222> LOCATION: (12)..(12)
<223> OTHER INFORMATION: His is  His(Trt):  S-trityl histine
<220> FEATURE:
<221> NAME/KEY: misc
<222> LOCATION: (15)..(15)
<223> OTHER INFORMATION: Cys is Cys(Acm):  Acetamidomethyl Cysteine
<220> FEATURE:
<221> NAME/KEY: misc
<222> LOCATION: (16)..(16)
<223> OTHER INFORMATION: Thr is Thr(tBu):  threonine tert-butyl ether
<220> FEATURE:
<221> NAME/KEY: misc
<222> LOCATION: (17)..(17)
<223> OTHER INFORMATION: Lys is Lys(Boc):  tertbutyloxycarbonyl lysine
<220> FEATURE:
<221> NAME/KEY: misc
<222> LOCATION: (18)..(18)
<223> OTHER INFORMATION: Arg is Arg(Pbf):
    2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu):  serine tert-butyl ether
<220> FEATURE:
<221> NAME/KEY: misc
<222> LOCATION: (22)..(22)
<223> OTHER INFORMATION: Arg is Arg(Pbf):
    2,2,4,6,7-pentamethyldihydrobenzofuran-5-sulfonyl arginine
<220> FEATURE:
<221> NAME/KEY: misc
<222> LOCATION: (24)..(24)
<223> OTHER INFORMATION: Cys is connected to Cys at position 11

<400> SEQUENCE: 26

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 27
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Arg is Arg(Pbf):
    2,2,4,6,7-pentamethyldihydrobenzofuran-5-sulfonyl arginine
<220> FEATURE:
<221> NAME/KEY: misc
<222> LOCATION: (3)..(3)
<223> OTHER INFORMATION: Tyr is Tyr(tBu):  tyrosine tert-butyl ether
<220> FEATURE:
<221> NAME/KEY: misc
<222> LOCATION: (8)..(8)
<223> OTHER INFORMATION: Glu is Glu(tBu):  glutamic acid tert-butyl
    ester
<220> FEATURE:
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is Cys(Trt):  S-trityl cysteine
```

```
<220> FEATURE:
<221> NAME/KEY: misc
<222> LOCATION: (11)..(11)
<223> OTHER INFORMATION: Cys is Cys(Trt): S-trityl cysteine
<220> FEATURE:
<221> NAME/KEY: misc
<222> LOCATION: (15)..(15)
<223> OTHER INFORMATION: Cys is Cys(Trt): S-trityl cysteine
<220> FEATURE:
<221> NAME/KEY: misc
<222> LOCATION: (16)..(16)
<223> OTHER INFORMATION: Thr is Thr(tBu): threonine tert-butyl ether
<220> FEATURE:
<221> NAME/KEY: misc
<222> LOCATION: (17)..(17)
<223> OTHER INFORMATION: Lys is Lys(Boc): tertbutyloxycarbonyl lysine
<220> FEATURE:
<221> NAME/KEY: misc
<222> LOCATION: (18)..(18)
<223> OTHER INFORMATION: Arg is Arg(Pbf):
     2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu): serine tert-butyl ether
<220> FEATURE:
<221> NAME/KEY: misc
<222> LOCATION: (22)..(22)
<223> OTHER INFORMATION: Lys is Lys(Boc): tertbutyloxycarbonyl lysine
<220> FEATURE:
<221> NAME/KEY: misc
<222> LOCATION: (23)..(23)
<223> OTHER INFORMATION: Tyr is Tyr(tBu): tyrosine tert-butyl ether
<220> FEATURE:
<221> NAME/KEY: misc
<222> LOCATION: (24)..(24)
<223> OTHER INFORMATION: Cys is Cys(Trt): S-trityl cysteine

<400> SEQUENCE: 27

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 28
<211> LENGTH: 24
<212> TYPE: PRT
<213> ORGANISM: Homo sapiens
<220> FEATURE:
<221> NAME/KEY: misc
<222> LOCATION: (19)..(19)
<223> OTHER INFORMATION: Ser is Ser(tBu): serine tert-butyl ether

<400> SEQUENCE: 28

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 29
<211> LENGTH: 24
<212> TYPE: PRT
<213> ORGANISM: Homo sapiens
<220> FEATURE:
<221> NAME/KEY: misc
<222> LOCATION: (1)..(1)
<223> OTHER INFORMATION: Glu is Glu(tBu): glutamic acid tert-butyl
     ester
<220> FEATURE:
<221> NAME/KEY: misc
<222> LOCATION: (3)..(3)
<223> OTHER INFORMATION: Tyr is Tyr(tBu): tyrosine tert-butyl ester
<220> FEATURE:
```

```
<221> NAME/KEY: misc
<222> LOCATION: (4)..(4)
<223> OTHER INFORMATION: Ser is Ser(tBu):  serine tert-butyl ether
<220> FEATURE:
<221> NAME/KEY: misc
<222> LOCATION: (8)..(8)
<223> OTHER INFORMATION: Asn is Asn(Trt): trityl Asparagine
<220> FEATURE:
<221> NAME/KEY: misc
<222> LOCATION: (9)..(9)
<223> OTHER INFORMATION: Lys is Lys(Boc):  tertbutyloxycarbonyl lysine
<220> FEATURE:
<221> NAME/KEY: misc
<222> LOCATION: (10)..(10)
<223> OTHER INFORMATION: Cys is  Cys(Trt):  trityl cysteine
<220> FEATURE:
<221> NAME/KEY: misc
<222> LOCATION: (11)..(11)
<223> OTHER INFORMATION: Cys is  Cys(Trt):  trityl cysteine
<220> FEATURE:
<221> NAME/KEY: misc
<222> LOCATION: (12)..(12)
<223> OTHER INFORMATION: His is  His(Trt):   S-trityl histine
<220> FEATURE:
<221> NAME/KEY: misc
<222> LOCATION: (15)..(15)
<223> OTHER INFORMATION: Cys is Cys(Trt):  trityl cysteine
<220> FEATURE:
<221> NAME/KEY: misc
<222> LOCATION: (16)..(16)
<223> OTHER INFORMATION: Thr is Thr(tBu):  threonine tert-butyl ether
<220> FEATURE:
<221> NAME/KEY: misc
<222> LOCATION: (17)..(17)
<223> OTHER INFORMATION: Lys is Lys(Boc):  tertbutyloxycarbonyl lysine
<220> FEATURE:
<221> NAME/KEY: misc
<222> LOCATION: (18)..(18)
<223> OTHER INFORMATION: Arg is Arg(Pbf):
     2,2,4,6,7-pentamethyldihydrobenzofuran-5-sulfonyl arginine
<220> FEATURE:
<221> NAME/KEY: misc
<222> LOCATION: (19)..(19)
<223> OTHER INFORMATION: Ser is Ser(tBu):  serine tert-butyl ether
<220> FEATURE:
<221> NAME/KEY: misc
<222> LOCATION: (22)..(22)
<223> OTHER INFORMATION: Arg is Arg(Pbf):
     2,2,4,6,7-pentamethyldihydrobenzofuran-5-sulfonyl arginine
<220> FEATURE:
<221> NAME/KEY: misc
<222> LOCATION: (24)..(24)
<223> OTHER INFORMATION: Cys is trityl cysteine

<400> SEQUENCE: 29

Glu Leu Tyr Ser Ala Leu Ala Asn Lys Cys Cys His Val Gly Cys Thr
1               5                   10                  15

Lys Arg Ser Leu Ala Arg Phe Cys
            20
```

PEPTIDE SYNTHESIS

RELATED APPLICATION

This application claims the benefit of Greek Application No. 20090100310, filed on Jun. 1, 2009, entitled "Peptide Synthesis" which is incorporated herein by reference.

BACKGROUND OF THE INVENTION

This invention relates to peptide synthesis, in particular to the synthesis of a peptide hormone. The invention relates especially to the synthesis of a peptide of the insulin family, particularly to the synthesis of relaxin.

Relaxin (RLX) was discovered in 1926 by Frederick Hisaw [Hisaw, F. (1926) Experimental relaxation of the pubic ligament of the guinea pig. Proc. Soc. Exp. Biol. Med. 23, 661-663] as a substance that could relax the pelvic ligaments and regulate the female reproductive tract functions. The relaxin family of peptides comprises the relaxin-1 (RLX1), relaxin-2 (RLX2) and relaxin-3 (RLX3). Relaxin peptides belong to the greater family of the insulin like peptides (INSL). This peptide family includes insulin and insulin like peptide 3, 4, 5 and 6. These peptides have a high degree of structural similarity.

In addition to the female reproductive tract function, relaxins are known to participate in a range of medical conditions for example in cardiac protection, as disclosed in Samuel, C. S. and Hewitson, T. D. (2006) Relaxin in cardiovascular and renal disease; Kidney Int. 69, 1498-1502; Bani, D., Nistri, S., Bani Sacchi, T. and Bigazzi, M. (2005) Basic progress and future therapeutic perspectives of relaxin in ischemic heart disease. Ann. N. Y. Acad. Sci. 1041, 423-430; Samuel, C. S., Du, X. J., Bathgate, R. A. D. and Summers, R. J. (2006) "Relaxin" the stiffened heart and arteries: the therapeutic potential for relaxin in the treatment of cardiovascular disease. Pharmacol. Ther. 112, 529-552; Dschietzig, T., Bartsch, C., Baumann, G. and Stangl, K. (2006) Relaxin—a pleiotropic hormone and its emerging role for experimental and clinical therapeutics. Pharmacol. Ther. 112, 38-56; in fibrosis as disclosed in Bathgate, R. A. D., Hsueh, A. J. and Sherwood, O. D. (2006) Physiology and molecular biology of the relaxin peptide family. In: Physiology of Reproduction. (Knobil, E. and Neill, J. D., Eds), 679-770. Elsevier, San Diego; Sherwood, O. D. (2004) Relaxins physiological roles and other diverse actions. Endocr. Rev. 25, 205-234; Samuel, C. S. (2005) Relaxin: antifibrotic properties and effects in models of disease. Clin. Med. Res. 3, 241-249; in allergic responses as disclosed in Bani, D. (1997) Relaxin: a pleiotropic hormone. Gen. Pharmacol. 28, 13-22.; in cancer as disclosed in Silvertown, J. D., Summerlee, A. J. and Klonisch, T. (2003) Relaxin-like peptides in cancer. Int. J. Cancer 107, 513-519; Kamat, A. A., Feng, S., Agoulnik, I. U., Kheradmand, F., Bogatcheva, N. V., Coffey, D., Sood, A. K. and Agoulnik, A. I. (2006) The role of relaxin in endometrial cancer. Cancer Biol. Ther. 5, 71-77; and in wound healing as disclosed in Yamaguchi, Y. and Yoshikawa, K. (2001) Cutaneous wound healing: an update. J. Dermatol. 28, 521-534; 113 Wyatt, T. A., Sisson, J. H., Forget, M. A., Bennett, R. G., Hamel, F. G. and Spurzem, J. R. (2002) Relaxin stimulates bronchial epithelial cell PKA activation, migration, and ciliary beating, Exp. Biol. Med. (Maywood) 227, 1047-1053; Casten, G. G. and Boucek, R. J. (1958) Use of relaxin in the treatment of scleroderma. J. Am. Med. Assoc. 166, 319-324.

Other therapeutic applications of RLX2 are believed to be associated with its ability to control collagen turnover as disclosed in Samuel C S, Hewitson T D, Unemori E N, Tang M L, Cell Mol Life Sci. 2007, 64, 1539-57. Drugs of the future: the hormone relaxin.

RLX2 potentially has a wide range of therapeutic applications and a significant demand exists for its use in research and for therapeutic purposes. The therapeutic potential of other relaxins has generally not been investigated due to difficulties in producing or isolating them.

RLX has two peptide chains, generally referred to as the A chain (RLXA) and the B chain (RLXB). The chains are joined by two intermolecular cysteine bridges and chain A contains an additional intramolecular disulphide bond. The conformational arrangement of the chains is an important feature of relaxins particularly RLX1 and RLX2 and the two chains must be connected with the appropriate disulphide bonds in order to exhibit the appropriate biological activity. Furthermore RLXB is generally highly insoluble in aqueous solution. The insolubility of RLXB and the need to ensure the appropriate disulphide bonds are formed means synthesis by random chain combination is very difficult and makes the purification of RLXB, for example by chromatographic methods, very difficult, as disclosed in J.-G. Tang et al, Biochemistry 2003, 42, 2731-2739; Wade, J. D., and Tregear, G. W. (1997) Relaxin. Methods Enzymol. 289, 637-646.

Methods of production of relaxins using recombinant DNA techniques have been disclosed in U.S. Pat. Nos. 4,758,516 and 5,023,321 a division of U.S. Pat. No. 4,758,516. In these patents, genes and DNA transfer vectors for the expression of human preprorelaxin and subunits thereof including genes and transfer vectors for the expression of human prorelaxin and the A, B and C chains are disclosed with methods for synthesis of the peptides using recombinant DNA techniques.

U.S. Pat. No. 5,464,756 discloses a process for cleaving a peptide into two polypeptide components by treating a reduced free-cysteine form of the polypeptide with a cleaving agent and in particular culturing cells containing DNA encoding the polypeptide and having at least one Asp codon present at the position to be cleaved such that DNA is expressed to produce the polypeptide in the host cell culture and treating the free-cysteine form of the polypeptide with dilute acid to effect the desired cleavage.

Recombinant DNA techniques may be lengthy and complex and unsatisfactory for production of relaxins on a large scale. Furthermore, as materials used in the techniques are animal-based, objections to the use of relaxins produced by such methods may arise on religious grounds or for ethical reasons, limiting the utility of relaxin products produced in this way.

Chemical synthesis of relaxins generally has proved problematic. Chemical synthesis of RLX1 is not known and consequently nor is the investigation of possible therapeutic uses of synthetic RLX1.

E. Bullesbach and C. Schwabe, Journal Biol. Chem. 1991, 266, 10754-10761; E. Bullesbach and C. Schwabe, J. Biol. Chem. 2005, 280, 14586-14590 discloses the chemical synthesis of RLX 2. This process involves the solid phase synthesis of the two individual chains and their site directed combination that is protecting a specific cysteine residue to ensure pre-determined cysteine residues combine to form a specific disulphide link. After the assembly of the chains, two reaction steps requiring the application of hydrogen fluoride and three reaction steps for the site directed chain combination are needed for the completion of the synthesis of RLX2. This method is however, very laborious, has poor yields and undesirably requires the use of highly toxic and hazardous hydrogen fluoride.

U.S. Pat. No. 4,835,251 discloses a method for combining an A chain of human relaxin and a B chain of human relaxin to produce biologically active human relaxin by mixing a reduced free-cysteine form of the A chain and a reduced free-cysteine form of the B chain in an aqueous medium at a pH of 7 to 12 under oxygen wherein the B chain, but not the product, is denatured.

Attempts to produce synthetic human relaxins have however not yielded satisfactory results. Chain B of human relaxin-1 (RLX1B) and of human relaxin-2 (RLX2B) and intermediate smaller peptides and fragments are highly insoluble or hydrophobic and difficulties have been encountered in extending the peptide chain around the sequence Ala-Gln-Ile-Ala-Ile-Cys (SEQ ID NO:1) of RLX1B and RLX2B. Solid phase synthesis routes involve very difficult coupling and deprotection steps. Furthermore, difficulties are encountered in forming the appropriate interchain disulphide Bond combinations for RLX1B and RLX2B with the corresponding relaxin A-chains due to the insolubility of the B chains leading to undesirable precipitation or non-dissolution of B chains during synthesis of the relaxin.

SUMMARY OF THE INVENTION

A need exists for a method of producing insulin-type peptides, for example relaxins, especially human relaxins, without using recombinant DNA techniques and which does not involve a lengthy or complex process or the use of hazardous reagents. Further, production of relaxins without resorting to recombinant DNA techniques would provide a source of material and be especially beneficial in enabling potential therapeutic applications to be investigated.

We have now developed a synthetic route for the production of insulin-type peptides by utilising the higher solubility of B-chains of insulin-type peptides and relaxins which contain at least one methionine sulphoxide residue especially relaxin 1 and relaxin 2, relaxin-type products and their precursors, for example, the B-chain of relaxins.

In particular, the present application provides an improved chemical synthesis of RLX2 (the structure of which is shown in FIG. 2), and novel chemical synthesis of RLX1 (the structure of which is shown in FIG. 1), RLX1B, RLX2B and Met(O)$^{24}$-RLX1B and Met(O)$^{25}$-RLX2B (the structures of which are as shown in FIGS. 5 and 6, respectively).

In one embodiment, there is provided a process for the production of an insulin-type peptide having at least two peptide chains, A and B, chain A and chain B being linked by at least one disulphide link which process comprises providing peptide chain A and chain B, each chain containing at least one cysteine residue and at least one of chain A and chain B containing an oxidised methionine residue, combining chain A and chain B under conditions such that at least one cysteine residue in chain A and at least one cysteine residue in chain B combine to link the chains together and reducing the oxidised methionine residue to produce the insulin-type peptide.

Suitably the insulin-type peptide is a relaxin, for example relaxin-1 and relaxin-2 and chain A is a relaxin A-chain and chain B is a relaxin B-chain. Suitably, the oxidised methionine residue is a methionine oxide residue, and the residue is in the B-chain.

In another embodiment, there is provided a process for the production of a biologically active relaxin comprising providing a relaxin A-chain having at least one intramolecular disulphide link and a relaxin B-chain wherein at least one methionine residue of the B-chain has been oxidised, the B-chain optionally containing an intramolecular disulphide link, combining the A-chain and the B-chain under conditions such that at least one intermolecular disulphide link is formed between the A-chain and the B-chain to link the chains together and reducing the oxidised methionine residue to produce the relaxin.

In one aspect of the application, the relaxin is human relaxin and in a particular aspect, the relaxin is human relaxin 1 wherein the B-chain is Met(O)$^{24}$RLX1B or human relaxin 2 wherein the B-chain is Met(O)$^{25}$RLX2B.

In another aspect, the B-chain of a relaxin containing one or more methionine sulphoxide residues exhibits higher solubility than the corresponding B-chain of a relaxin which does not have a methionine sulphoxide residue. In particular, human Met(O)$^{24}$-RLX1B and human Met(O)$^{25}$-RLX2B have higher solubility properties than RLX1B and RLX2B chains respectively. The higher solubility of the methionine sulphoxide analogue enables facile synthesis of relaxins and the B-chain and purification and application in interchain combination reactions to produce a biologically active relaxin.

Suitably, the interchain combination reaction is carried out in aqueous solution at room temperature and neutral or desirably alkaline pH. The interchain reaction may be carried out in the presence of an oxidising agent or a reducing agent. The reduced form of the B-chain that is with free cysteine groups, may act to catalyse the inter-chain reaction and a separate oxidising agent or reducing agent may not be required. In another aspect, the A-chain is present in at least a stoichiometric equivalent level to the B-chain and desirably is in stoichiometric excess, desirably, on a molar basis, greater than 1:1 to 3:1 and preferably 1.01 to 2:1.

The oxidised methionine residue may be reduced using any known reducing agent suitable for reduction in peptide synthesis and desirably which is specific to the reduction of a methionine oxide residue. Iodide, for example ammonium iodide is preferred.

In another embodiment for carrying out the inter-chain reaction, the relaxin A-chain is suitably in bicyclic form and the methionine-oxidised relaxin B-chain is in cyclic form or in a fully reduced form.

In a further aspect, there is provided synthetically produced human relaxin 1, the structure of which is shown in FIG. 1, and a pharmaceutically acceptable salt, derivative or prodrug thereof.

In a further aspect, the application discloses a process for the production of an insulin-type peptide having at least two peptide chains, A and B, chain A and chain B being linked by at least one disulphide link and chain B having at least one oxidised methionine residue, which process comprises providing peptide chain A and chain B, each chain containing at least one cysteine residue and chain B containing an oxidised methionine residue, combining chain A and chain B under conditions such that at least one cysteine residue in chain A and at least one cysteine residue in chain B combine to link the chains together to produce the insulin-type peptide having an oxidised methionine residue.

In another embodiment, the application further provides a biologically active, synthetic insulin-type polypeptide containing one or more methionine sulphoxide residues, for example human Met(O)$^{24}$-relaxin 1 having a sequence as illustrated in FIG. 3 and human Met(O)$^{25}$-relaxin 2 having a sequence as illustrated in FIG. 4, and a pharmaceutically acceptable salt, derivative or prodrug thereof. In one aspect, the synthetic insulin-type polypeptide is a relaxin. In another aspect, the synthetic insulin-type polypeptide is a human relaxin.

The relaxin A chain may be produced by a range of methods optionally including the use of known protecting groups in synthesising the peptide chain and the chain is suitably subjected to a cyclisation reaction wherein one or more intramolecular disulphide links are formed, for example as set out in FIGS. 9 to 14.

The application further provides a synthetic chimeric polypeptide comprising whole or part of a polypeptide sequence of a synthetic relaxin and a polypeptide sequence not derived from a relaxin.

The application also provides a synthetic polypeptide comprising whole or part of a polypeptide sequence of a synthetic relaxin, preferably a B-chain of a synthetic relaxin, and optionally containing one or more methionine sulphoxide residues.

The insulin-type peptides of the embodiments and aspects described herein are suitable for use in therapeutic applications.

The present application also provides for a synthetic insulin-type polypeptide, including a human relaxin, and a synthetic polypeptide and pharmaceutically acceptable salt, derivative or prodrug thereof for use in a method of treatment of the human or animal body by therapy, especially in one or more of providing cardiac protection, treatment of a cardiac condition, fibrosis, allergic response, cancer and in wound healing and in treating a condition requiring control of collagen turnover.

In a further aspect, there is provided a pharmaceutical composition comprising a synthetic polypeptide, preferably a synthetic relaxin, for example synthetic relaxin-1, synthetic relaxin-2 and a synthetic relaxin having at least one methionine sulphoxide residue, and a pharmaceutically acceptable carrier.

The higher solubility of insulin-type polypeptides having a methionine sulphoxide residue as compared to their analogues without the sulphoxide affords greater flexibility in formulation, renders them especially suitable for use in formulating a pharmaceutical composition and may provide enhanced bioactivity as well as having desirable characteristics to allow formation of a synthetic relaxin.

Suitably, the methionine sulphoxide residue, denoted herein as "Met(O)", may be introduced in the peptide chain at the required positions using N-protected Met(O) derivatives known in the art.

The invention and representative synthetic routes are illustrated in the accompanying figures in which:

FIG. 1 shows the structure (sequence) of synthetic human Relaxin 1 (shRLX1) (The amino acid sequences of A-chain and B-chain of shRLX1 are shown in SEQ ID NOs: 2 and 3, respectively.);

FIG. 2 shows the structure (sequence) of synthetic human Relaxin 2 (shRLX2) (The amino acid sequences of A-chain and B-chain of shRLX2 are shown in SEQ ID NOs: 4 and 5, respectively.);

FIG. 3 shows the structure (sequence) of B-Met(O)$^{24}$-synthetic human Relaxin 1 (B-Met(O)$^{24}$shRLX1) (The amino acid sequences of A-chain and B-chain of B-Met(O)$^{24}$shRLX1 are shown in SEQ ID NOs: 2 and 6, respectively.);

FIG. 4 shows the structure (sequence) of B-Met(O)$^{25}$-synthetic human Relaxin 2 (B-Met(O)$^{25}$shRLX2) (The amino acid sequences of A-chain and of B-chain of B-Met(O)$^{25}$shRLX2 are shown in SEQ ID NOs: 4 and 7, respectively.);

FIG. 5 shows DMSO oxidation; Synthesis of reduced (linear) Met(O)$^{24}$-human relaxin 1 B-chain [compound 9, Met(O)$^{24}$-shRLX1B], of oxidized (cyclic) Met(O)$^{24}$-human relaxin 1 B-chain [compound 10, Met(O)$^{24}$-shRLX1B] and of oxidized (cyclic) human relaxin 1 B-chain [compound 11, shRLX1B] (The amino acid sequences of compounds 6, 7, 8, 9, 10 and 11 are shown in SEQ ID NOs: 8, 9 10, 6, 6 and 3, respectively);

FIG. 6 shows DMSO oxidation Synthesis of reduced (linear) Met(O)$^{25}$-human relaxin 2 B-chain [compound 13, Met(O)$^{25}$-shRLX2B], of oxidized (cyclic) Met(O)$^{25}$-human relaxin 2 B-chain [compound 14, Met(O)$^{25}$-shRLX2B] and of oxidized (cyclic) human relaxin 2 B-chain [Compound 15, shRLX2B] (The amino acid sequences of compounds 6, 7, 12, 13, 14 and 15 are shown in SEQ ID NOs: 8, 9 11, 7, 7 and 5, respectively);

FIG. 7 shows Iodine oxidation; Synthesis of oxidized (cyclic) Met(O)$^{24}$-human relaxin 1 B-chain [compound 10, Met(O)$^{24}$-shRLX1B] (The amino acid sequences of compounds 10, 16, and 17 are shown in SEQ ID NOs: 6, 12 and 13, respectively);

FIG. 8 shows Synthesis of oxidized (cyclic) Met(O)$^{25}$-human relaxin 2 B-chain [Compound 14, Met(O)$^{25}$shRLX2B] (The amino acid sequences of compounds 14, 18, and 19 are shown in SEQ ID NOs: 7, 14, and 14, respectively);

FIG. 9 shows Synthesis of bicyclic RLX1A [compound 24] with the application of S-Mmt and Trt protecting groups (The amino acid sequences of compounds 21, 22, 23, and 24 are shown in SEQ ID NOs: 15, 16, 17, and 18, respectively);

FIG. 10 shows Synthesis of bicyclic human relaxin 2 chain A [compound 28; bicyclic RLX2A] with the application of S-Mmt and Trt protecting groups (The amino acid sequences of compounds 25, 26, 27, and 28 are shown in SEQ ID NOs: 19, 20, 21 and 22, respectively);

FIG. 11 shows Synthesis of bicyclic human relaxin 1 chain A [RLX1A-chain; compound 24; bicyclic RLX1A] with the application of S-Acm and Trt protecting groups (The amino acid sequences of compounds 29 and 30 are shown in SEQ ID NOs: 23 and 24, respectively);

FIG. 12 shows Synthesis of bicyclic human relaxin 2 chain A [compound 19; bicyclic RLX2A] with the application of S-Acm and Trt protecting groups (The amino acid sequences of compounds 31 and 32 are shown in SEQ ID NOs: 25 and 26, respectively);

FIG. 13 shows Synthesis of a mixture of bicyclic synthetic human relaxin 1 chains A [compounds 24, 35-36; bicyclic RLX1A] by the DMSO oxidation of the linear chain relaxin 1 chain A (The amino acid sequences of compounds 33, 34, 35 and 36 are shown in SEQ ID NOs: 27, 28 17 and 17, respectively);

FIG. 14 shows Synthesis of a mixture of synthetic human relaxin 2 chain A [compounds 28, 39-40; bicyclic RLX2A] by the DMSO oxidation of linear chain relaxin 2 chain A (The amino acid sequences of compounds 37, 38, 39 and 40 are shown in SEQ ID NOs: 29 22, 22 and 22, respectively);

FIG. 15 shows examples of resins of the trityl and benzhydryl-type used for the synthesis of RLXs A- and B-chains;

FIG. 16 shows Synthesis of Met(O)$^{24}$-Relaxin 1 [Met(O)$^{24}$-RLX1; compound 3] and of Relaxin 1 [RLX1; compound 1] by chain combination of bicyclic RLX1A and reduced Met(O)$^{24}$-RLX1B-chains;

FIG. 17 shows Synthesis of Met(O)$^{24}$-Relaxin 1 [Met(O)$^{24}$-RLX1] by chain combination of bicyclic RLX1A and cyclic RLX1B-chains and a small amount of linear RLX1B-chain;

FIG. 18 shows Synthesis of Met(O)$^{25}$-RLX2] and of RLX2 by chain combination of bicyclic RLX2A and reduced Met(O)$^{25}$-RLX2B;

FIG. 19 shows Synthesis of human relaxin 2 [RLX2; compound 2] and of Met(O)$^{25}$-human relaxin 2 [Met(O)$^{25}$-RLX2]; [compound 4] by chain combination of bicyclic RLX2A and cyclic Met(O)$^{25}$-RLX2B) and a small amount of linear RLX2B-chain.

Derivatives may include Fmoc-Met(O)—OH, Boc-Met(O)—OH and Trt-Met(O)—OH as illustrated in FIGS. 5 to 8, and as provided herein.

Preparation of a Met(O) containing RLXB may suitably be carried out by the on-resin oxidation of the Met residues as illustrated in FIGS. 5 and 6. This process is suitably carried out employing an oxidising agent and a solvent. In one particular aspect, the oxidising agents include hydrogen peroxide and 2-chlorobenzoyl peroxide. Suitably an organic solvent, for example tetrahydrofuran is employed.

FIGS. 5 and 6 illustrate examples of the synthesis of Met(O)$^{24}$-human Relaxin 1 B-chain [Met(O)$^{24}$-hRLX1B] and of the corresponding sequence of Met(O)$^{25}$-human Relaxin 2 B-chain [Met(O)$^{25}$-hRLX2B].

RLX2B may contain a Met(O) at position 25, of the peptide chain, at position 4 of the peptide chain or at both positions 4 and 25 as desired. RLX2B containing Met(O) only at position 4 reveals also a higher solubility comparing to the non-oxidised analogue. In one aspect, the present application enables formation of the correct intramolecular and intermolecular disulphide bonds in relaxins.

Oxidation of the cysteine thiol groups to form the intramolecular disulphide bonds may be accomplished using any suitable oxidant but preferably using DMSO (J. P. Tam, et al. J. Am. Chem. Soc. 1991, 113, 6657-6662) especially where the RLXA and RLXB-chains are unprotected, for example as shown in FIGS. 5 and 6 and with iodine in the cases where the oxidation is carried out with protected or partially protected peptides as shown in FIGS. 7-12.

Suitably the A-chain and the B-chain of the relaxin are purified. The reaction, suitably an oxidising reaction, to which the cysteine residues are subjected to form the intramolecular disulphide link may be carried out before or after purification of the individual A-chain and/or B-chain.

In synthesising the peptide, known protecting groups may be employed as desired. The protecting groups may be removed prior to the formation of the disulphide bond or may be retained and the disulphide link may be formed with the peptide in the protected form. Standard protecting groups that may be employed in peptide synthesis are disclosed, for example, in Barany and Merrifield in "The Peptides" Vol. 2, Ed. Gross and Minehoffer, Academic Press, pp. 233-240 (1980), the disclosure of which is incorporated herein.

Syntheses of either or both the A-chain and B-chain may be carried out on a solid support. Formation of the disulphide bond may take place on the resin, after cleavage of the peptide from the resin or simultaneously with its cleavage from the resin as desired.

Suitably, the thiol group of the cysteine residue may be protected during the peptide assembly process employing any protecting group known in the art of thiol protection. Preferably 4-methoxytrityl (Mmt) (Barlos et al. Int J Pept Protein Res. 1996, 47, 148-53), trityl (Trt) and acetamidomethyl (Acm) groups are used.

In addition to the surprising improvement of solubility of the B-chain due to the presence of the oxidised methionine residue, further improvements in solubility of the A-chain and the B-chain may be achieved. Once the intramolecular disulphide bonds have been formed, elution of the cyclic chain is more rapid on analytical and preparative HPLC, as compared to the corresponding reduced peptides and also of other impurities. Higher level purity may be obtained for the A-chain and B-chain having intramolecular disulphide links (i.e., the cyclic INSL peptides) as compared to a corresponding linear A-chain and B-chain. Accordingly, higher purity may be obtained from the cyclic INSL peptides than can be obtained from the individual A-chain and B-Chain. In certain aspects, the cyclic INSL peptides are obtained at greater than 95%, greater than 96%, greater than 97%, greater than 98%, and greater than 99% pure.

For the selective formation of the intramolecular disulphide bridges in chain A any orthogonal thiol protecting group pair may be used but one of the Trt/Mmt, Trt/Acm and Mmt/Acm pairs is preferable. Examples of the preparation of bicyclic chain A of RLX1 and RLX2 are shown in FIGS. 9 to 12.

In the case of using the Trt/Mmt pair the S-Mmt group may be selectively removed followed by the formation of the disulphide bonds between the liberated thiol functions by their oxidation with an appropriate oxidizing agent, such as DMSO or air as shown in FIGS. 9 to 10. Removal of the S-Trt-groups and the oxidation of the liberated thiol functions suitably lead to the formation of the second disulphide bond. Preferably the second disulphide bond is created by the oxidative removal of the S-Trt or S-Acm groups with iodine. By using the 2-chlorotrtyl resin (K. Barbs et al, Int. J. Pept. Protein Res. 1991, 37, 513-520) or a resin with similar acid sensitivity for the solid phase synthesis of A chains, the selective removal of the S-Mmt functions by mild acidolysis is suitably performed simultaneously with the cleavage of the protected peptide from the resin.

For the oxidative removal of the S-Trt-function followed by disulphide bond formation any oxidant known in the art can be used but preferably iodine.

Where the Trt/Acm pair is employed, the S-Trt group may be selectively removed in the presence of S-Acm groups by the acidolytic treatment of the peptide resin with a solution of an appropriate acid, preferably trifluoroacetic acid in dichloromethane in 10-100% concentration in trifluoroacetic acid and suitably the addition of scavengers preferably thiols, silanes and water in effective proportions. The formation of the first disulphide bond is then suitably achieved by oxidation with any oxidizing agent known in the art preferably with DMSO or air.

The formation of the first disulphide bond may also be achieved by using iodine for the oxidative removal of the S-Trt-functions where present. This may occur before, during or after the cleavage of the protected peptide from the resin (K. Barlos et al, Int. J. of Peptide & Protein Research, 1991, 38, 562-568).

Suitably, and without wishing to be bound by any theory, the required disulphide bond is created selectively in the presence of the S-Acm groups if the iodolysis is performed at low temperatures for example, 0° C. to 15° C. Suitably the reaction is carried out in a lypophilic solvent preferably a chlorinated hydrocarbon for example dichloromethane, and fluorinated alcohol for example trifluoroethanol, and a mild acid for example acetic and trifluoroacetic acid as illustrated in FIGS. 11-12.

In another embodiment, the second disulphide bond may be formed by iodolysis in more polar solvents by adding polar components for example acetic acid, methanol, trifluoroethanol, trifluoroacetic acid or/and water in the reaction mixture. The temperature during oxidation, preferably during iodolysis, is not critical but is preferably carried out at 5 to 25° C. range.

Suitably, the relaxins are synthesised in the solid phase. In a preferred embodiment, any resin known in the art may be employed but preferably the synthesis is carried out on a resin or linker of the trityl type for example 2-chlorotrityl-chloride resin as shown in FIG. 15 (K. Barlos, et al., Tetrahedron Lett., 1989, 30, 3943; K. Barlos, et al., Tetrahedron Lett., 1989, 30, 3947; K. Barlos, et al., Angew. Chem. Int. Ed. Engl., 1991, 30, 590; K. Barlos, et al., Int. J. Pept. Protein Res., 1991, 37, 513; K. Barlos, et al., Int. J. Pept. Protein Res., 1991, 38, 562) and the 4-methylbenzhydryl-bromide resins a in FIG. 15 (K. Barlos et al, Liebigs Annalen der Chemie (1989), (10), 951-5).

It is known to employ expensive low loaded polystyrene-Peg-resins for the corresponding syntheses (E. Bullesbach and C. Schwabe). J. Biol. Chem. 266, 17, 10754-10761, 1991). However these resins have the drawback that the cysteine is susceptible to racemisation. This leads to complication and significantly higher costs due to the need to separate the D-diastereomeric peptides formed by Cys-racemisation during esterification and chain assembly. In addition, the cleavage of the peptides synthesised is not quantitative from other known resins leading to higher production cost.

In another embodiment, there is provided a process for the production of RLX1A or RLX2A in a solid phase synthesis using a resin or linker of the trityl type for example 2-chlorotrityl-chloride resin and the 4-methylbenzhydryl-bromide resin.

In the present application, the use of these resins is described for the preparation of RLX1A and RLX2A which both contain a Cys residue at their carboxyl-terminal position. Advantageously, these resins are highly preferable over other resins used in the art because no or minimal racemisation of the cysteine residue is observed. The carboxylate species is suitably formed rather than the acid species for reacting with the resin, especially with trityl and benzhydryl type resins. Further, quantitative cleavage of the peptide from the resin may be achieved (Fujiwara et al, Chem. Pharm. Bull. 42, 724, 1994).

In forming the relaxin, A-chain and a B-chain is combined under conditions effective to form an intermolecular disulphide bond and to provide the desired conformation of the relaxin to provide biological activity.

In general, and without wishing to be bound by any theory, the intramolecular disulphide bonds containing cyclic peptides (see compounds 10, 11, 14 and 15 in FIGS. 5 to 8) react faster than the corresponding linear peptides when forming the interchain —S—S— bonds. The cyclic peptides would appear to behave like activated cyclic peptides and undergo the interchain linking with the second chain in a more facile manner.

Suitably, linear chain peptides of chain A are oxidised for example with DMSO, air or other oxidant to produce a mixture of cyclic chain A isomers as illustrated in FIGS. 13 and 14. Cyclic relaxin chain B may be similarly produced from linear relaxin chain B. The relaxin may be formed by a mixture of isomers of bicyclic chains A or any of the pure bicyclic isomers reacting with chain B in cyclic or linear form. Suitably, the reaction or interaction between chain A and chain B is carried out in the presence of an oxidising agent or a reducing agent. Where linear chain A and especially linear chain B is present, no additional oxidising or reducing agent is required although this may be preferable. In another embodiment, the reaction/interaction between chain A and chain B is carried out in the presence of a reducing agent which may be referred to as a catalyst. Without wishing to be bound by any theory, it is believed that disulphide bridges are reduced to free thiols and an equilibrium of cyclic and interchain linked peptides is established which leads to the thermodynamically more stable products which are the native RLX proteins as shown in FIGS. 18 and 19.

As the reducing agent, any organic or inorganic reducing agent may be used but organic thiols for example, reduced chain A, reduced chain B, reduced glutathione, cysteine, thiophenol, thioanisole, pyridine-thiol, 3 or 5 nitropyridine-2-thiol, benzylmercaptam, dithiothreitol are employed. In another embodiment preferentially reduced chain-A, reduced chain-B or mixtures thereof may be used as the catalyst. The catalyst may be added in the mixture before, after or during the mixing of chain A and chain B.

The catalyst may be added in various amounts to build equilibration mixtures but may be added in an amount of 1 to 5% molar ratio calculated on the quantity of A chain and B chain. The temperature during the folding reaction in which the A-chain and B-chain combine is not critical but may be around room temperature, for example 20 to 25° C. Suitably, the solvent is an aqueous solution or a mixture of an aqueous and organic solvents and/or bases. The pH of the solution for the chain combination is not critical but preferentially is alkaline and desirably from 10 to 11.

Reduced chain A is suitably combined (folded) with chain B in the presence of an appropriate oxidant to promote formation of the desired RLX. Suitably, the reaction proceeds through the formation of mixtures of monocyclic and bicyclic chains A.

In another embodiment, oxidized chain A may be used as generally the reaction will be more rapid than where reduced chain A is employed. In one aspect, mixtures of the bi- and monocyclic chain A and chain B are reacted to provide the native RLXs.

In another embodiment, bicyclic chain A is combined with reduced chain B as shown in FIGS. 16 and 18 by adding DMSO, for example 15% DMSO, as the oxidant to promote the reaction. The molar ratio of chain A and B may be from 1:1 to 2:1, or the molar ratio of chain A and B may be 1.1:1 molar. The speed of the reaction may be increased with increasing the excess of chain A. Suitably excess of bi- and monocyclic chains A are recycled during purification for example by HPLC. Where an oxidant, for example DMSO, is not employed, the molar ratio of chain A to chain may be at least 4:1.

In another embodiment, where relaxin A-chain or relaxin B-chain is formed as a by-product in the interchain folding reaction, the by-product is subjected to oxidation to provide the oxidised methionine analogue which then suitably is able to participate as a reactant in a further interchain folding reaction.

Suitably, RLXs which contain Met(O) are reduced to the native proteins with a reducing agent for example ammonium iodide. Ammonium iodide is advantageous as it reduces selectively Met(O) to Met leaving intra- and intermolecular cysteine bridges intact. The reduction may be performed before or after purification of the A-chain and/or B-chain. Suitably, the reaction is almost quantitative. As the solvent, aqueous solutions or mixtures of aqueous with organic solvents may be used.

Purification of the RLX1A, RLX2A, RLX1B, RLX2B, RLX1, RLX2, Met(O)$^{24}$-RLX1 and Met(O)$^{25}$-RLX2 may be performed by HPLC using any suitable solvent but TFA, formic acid and acetic acid containing water and acetonitrile may be employed.

The purified RLX1A, RLX2A, RLX1B, RLX2B, RLX1, RLX2, Met(O)$^{24}$-RLX1 and Met(O)$^{25}$-RLX2 may suitably be isolated by lyophilisation or precipitation. Desalting if necessary is suitably performed using ion exchange resins for example Dowex.

Therapeutic Applications:

All relaxin analogues prepared herein have been tested and have been demonstrated to have biological activity similar to those of recombinant prepared relaxin-2. Therapeutic applications of the relaxin compounds prepared according to the methods described herein include the treatment of: pancreatitis; see Cosen-Binker L I et al, World K. Gastroenterol. 2006, 12:1558-1568; preeclampsia; see Mohaupt, M. Mol. Aspects Med. 2007, 28: 169-191; arthritis; see K. Santora et al, J. Pharmacol. Exp. Ther. 2007, 322: 887-893; endometrial angiogenesis; J. E. Girling et al, Angiogenesis, 2005; 8: 89-99; acute heart failure; see S. L. Teichman et al, Heart fail. Rev. 2009; 14: 321-329; cardiac anaphylaxis and as a novel anti-anaphylactic agent; see Daniele Bani, et al., Curr Allergy Asthma Rep. 2006 February; 6 (1):14-9, 16476189; the slowing of progression of renal disease by decreasing renal interstitial fibrosis; see S L Garber, Y Mirochnik, et al.; Kidney Int. 2001 March; 59 (3):876-82, 11231342; age-related progression of pulmonary fibrosis; see Chrishan S Samuel, et al., FASEB J. 2003 January; 17 (1):121-3, 12424226; asthma-like reaction; see D Bani, et al., Endocrinology. 1997 May; 138 (5):1909-15, 9112386; control of growth of human breast cancer cells; see M. Bigazzi et al, Cancer. 1992 Aug. 1; 70 (3): 639-43,1320450; management of scleroderma; R. K. Winkelmann, et al., Semin Cutan Med Surg. 2001 March; 20 (1):27-37, 11308134; and the treatment of anxiety, obesity and diseases involving fibrosis; see Emma T. van der Westhuizen et al, Drug Discovery Today, Volume 13, Issues 15-16, August 2008, Pages 640-651. All references cited in the present application disclosing the specific therapeutic applications and their methods of use are incorporated herein by reference in their entirety.

The present application is illustrated by the following non-limiting examples.

EXAMPLES

Example 1

Solid Phase Synthesis of Human RLX1A, RLX2A, Met(O)$^{24}$-RLX1B and Met(O)$^{25}$-RLX2B and of Their Protected Fragments. General Procedure.

A1. Preparation of Loaded 2-chlorotritylchloride (CTC) Resins; General Procedure:

CTC-Cl resin (100 g; loading 1.6 mmol/g) was charged to a 2 L peptide reactor and swelled with 700 mL DCM for 30 min at 25° C. The resin was drained and a solution of 100 mmol Fmoc-amino acid and of 300 mmol diisopropylethylamine (DIEA) in 500 mL of dichloromethane (DCM) was added. The mixture was stirred under nitrogen for 2 hours at a temperature of 25° C. Then, remaining active sites on the 2-CTC resins were end-capped with addition of 10 mL of MeOH for 1 hour. The resins were drained and washed twice with 400 mL dimethyl formamide (DMF). The resin was drained, and then treated twice with 500 mL of 25% by volume piperidine for 30 min. The resin was then washed with 500 mL DMF four times. The resin was de-swelled by washing with 3 times 500 mL isopropanol (IPA). The resin was dried to a constant weight. On the resin were loaded 70-95 mmol of the amino acid used.

A2. Preparation of Loaded 4-methylbenzhydryl bromide (MBH) Resins, General Procedure MBH-Br resin (100 g; 190 mmol) was charged to a 2 L peptide reactor and swelled with 700 mL DCM for 30 min at 25° C. The resin was drained and a solution of Fmoc-amino acid and DIEA in 500 mL of DCM was added. The mixture was stirred under nitrogen for 6 hours at a temperature of 25° C. Then, remaining active sites on the MBH resins were end-capped with addition of 10 mL of MeOH for 24 hours. The resin was drained and washed twice with 400 mL DMF. The resin was drained, and then treated twice with 500 mL of 25% by volume piperidin for 30 min. The resin was then washed with 500 mL DMF four times. The resin was de-swelled by washing with 3 times 500 mL IPA. The resin was dried to a constant weight in vacuum (15 Torr, 25° C.). On the resin were loaded 60-90 mmol of the amino acid used.

B. Solid Phase Step-Wise Synthesis, General Protocol:

Solid phase synthesis was carried out at 24° C., starting with 1.0 g each of amino acid-CTC resin or MBH resin, loaded as shown in Part A of this Example 1. For the synthesis the following protocol was used throughout:

B1. Swelling of the Resin:

The resin was placed in a 15 ml solid phase reactor and treated twice with 7 mL N-methyl pyrollidine (NMP) and drained.

B2. Activation of Amino Acid

The Fmoc amino acid (3.0 equivalents) and 1-hydroxybenzotriazole (4.0 equiv.) were weighed, dissolved in a reaction vessel with 2.5 times the volume of NMP and cooled to 0° C. Then, diisopropylcarbodiimide (DIC) (3.0 equiv.) were added and the mixture was stirred for 15 min.

B3. Coupling

The resulting B2 solution was added to the reactor of B1. The flask was rinsed with 1.0 times volume of DCM and added to the reactor, which was then stirred for 1-3 hours at 25-30° C. A sample was taken for Kaiser Test to check the reaction for completion. If the coupling reaction was incomplete after 3 hours (positive Kaiser Test), the reaction vessel was drained and recoupling was performed with fresh solution of activated amino acid. After completion of the coupling reaction, the coupling solution was drained and the resin was washed with NMP 4 times (5 vol. each wash).

B4. Fmoc-group Removal

The resin obtained in B3 was drained, and then treated twice with 5 mL of 25% by volume piperidine for 30 min. The resin was then washed with 5 mL NMP three times.

B5. Peptide Chain Elongation

After the completion of the introduction of every amino acid, the steps B2 to B5 were repeated until the completion of the peptide chain.

For the introduction of the individual amino acid, the following Fmoc-amino acid derivatives were used: Fmoc-Gly-OH, Fmoc-Ala-OH, Fmoc-Val-OH, Fmoc-Ile-OH, Fmoc-Leu-OH, Fmoc-Met-OH, Fmoc-Met(O)—OH, Fmoc-Phe-OH, Fmoc-Pro-OH, Fmoc-Asp(tBu)-OH, Fmoc-Glu(tBu)-OH, pGlu, Fmoc-Lys(Boc)-OH, Fmoc-Ser(tBu)-OH, Fmoc-Ser(Trt)-OH, Fmoc-Thr(tBu)-OH, Fmoc-Thr(Trt)-OH, Fmoc-Tyr(tBu)-OH, Fmoc-Tyr(Clt)-OH, Fmoc-Asn-OH, Fmoc-Asn(Trt)-OH, Fmoc-Gln-OH, Fmoc-Gln(Trt)-OH, Fmoc-Trp-OH, Fmoc-Trp(Boc)-OH, Fmoc-Arg(Pbf)-OH, Fmoc-His(Trt)-OH, Fmoc-Cys(Trt)-OH, Fmoc-Cys(Mmt)-OH and Fmoc-Cys(Acm)-OH and the following Boc-amino acids: Boc-Arg(Pbf)-OH, Boc-Gln-OH, Boc-Gln(Trt)-OH, Boc-Lys(Boc)-OH and Boc-Asp(tBu)-OH.

C. Cleavage of the Side Chain Protected RLXA and RLXB and of Their Protected Fragments Both Containing at the N-Terminus Fmoc- or Boc-Groups from the CTC-Resin, General Procedure.

The resin-bound peptide or peptide fragment, obtained as described above under B1-B5 was washed with 5 mL NMP 4 times, 5 ml IPA 3 times and finally with 7 ml DCM 5 times to remove any NMP or other basic contaminants. The resin was then cooled to 0° C. The DCM was drained and the resin was treated twice with a precooled at 5° C. solution of 10 mL 1% trifluoroacetic acid (TFA)/DCM, stirred for 20 min at 0° C. and filtered. The resin was then washed three times with 10 mL DCM. Pyridine was then added to the combined filtrates (1.3 equiv. in respect to TFA) to neutralize TFA. The DCM cleavage solution was then combined with the equal volume of water in respect to DCM. The resultant mixture was distilled under reduced pressure to remove DCM (350 Torr at 28° C.). The peptide or the peptide fragment precipitated out from the water when DCM was removed. The fragment was washed with water and dried at 30-35° C. under 15 Torr vacuum.

Example 2

Deprotection of Linear Reduced RLX1A, RLX2A, Met(O)$^{24}$-RLX1B and Met(O)$^{25}$-RLX2B and of Their Derivatives. General Procedure The protected RLX-chains A obtained as described above in the example 1 (0.01 mmol) was treated with a mixture 10 mL of TFA/dithiothreitol (DTT)/water (90:5:5) for three hours at 5° C. and for one hour at 15° C. The resulting solution was then concentrated in vacuum and precipitated by the addition of diisopropylether and washed three times with 10 ml diisopropylether. The obtained solid was then dried in vacuum (25° C., 15 Torr) to constant weight. The procedure was repeated with the protected RLX chains B with oxidised methionine groups.

Example 3

Deprotection of Mono and Bicyclic RLX1A, RLX2A, Met(O)$^{24}$-RLX1B and Met(O)$^{25}$-RLX2B. General Procedure:

The protected RLX obtained as described above in Example 1 (0.005 mmol) was treated with a mixture of 5 mL of TFA/triisopropylsilane (TIPS)/anisole/water (91:4:1:4) for three hours at 5° C. and for one hour at 15° C. The resulting solution was then concentrated in vacuum and precipitated by the addition of diisopropylether and washed three times with 5 ml diisopropylether. The obtained solid was then dried in vacuum (25° C., 15 Torr) to constant weight. The procedure was repeated for each chain A and chain B.

Example 4

Purification of Deprotected RLX1A, RLX2A, Met(O)$^{24}$-RLX1B and Met(O)$^{25}$-RLX2B and of Their Mono and Bicyclic Derivatives, General Procedure:

The crude deprotected trifluoroacetic acid salt of RLX1AMet(O)$^{24}$ Met(O)$^{25}$ was dissolved in 25% Acetonitrile in water and loaded on a semi preparative 10×25 mm column. Lichrospher 100, RP-18, 12 micron (Merck); Phase A=1%-TFA in acetonitrile, phase B=1%-TFA in water; Gradient=linear gradient of 25%-A to 65%-A in 30 min. The purification yields vary from 30-80%. The procedure was repeated for RLX2A, Met(O)$^{24}$-RLX1B and Met(O)$^{25}$-RLX2B and of their mono and dioxidized derivatives.

Example 5

Cleavage from the CTC-resin and simultaneous monooxidation of protected peptides with iodine. Preparation of monooxidized human relaxin A and B-chains, Met(O)$^{24}$-RLX1B and Met(O)$^{25}$-RLXB and of their fragments (FIG. 7 (compounds 16 to 17), 8 (compounds 18 to 19), 11 (compounds 29 to 30), and 12 (compounds 31 to 32)).

The N- and side chain protected resin-bound peptide or peptide fragment, obtained as described above in Examples 1 and 2 was washed with 5 mL NMP 4 times, 5 ml IPA 3 times and finally with 7 ml DCM 5 times to remove any NMP or other basic contaminant. The resin was then cooled to 0° C. The DCM was drained and the resin was than treated twice with a precooled at 5° C. solution of 10 mL 1%-TFA in DCM containing 10 equivalents iodine in respect to the resin bound peptide, stirred for 5 min at 0° C. and filtered (instead of 1% TFA the same volume on mixtures of dichloromethane/acetic acid/trifluoroethanol can be used as the solvent with similar results). The resin was then washed three times with 10 mL DCM. The combined filtrates were then warmed at 15° C. and stirred for additional 30 min. Pyridine was then added (1.3 equiv. in respect to TFA) to neutralize TFA. The DCM cleavage solution was then combined with an equal volume of 3%-sodiumthiosulfate or ascorbic acid in water in respect to DCM to destroy excess iodine. That is indicated by the decolourization of the mixture. The resulting mixture was then distilled under reduced pressure to remove DCM (350 Torr at 28° C.). The protected peptide or peptide fragment precipitated out from the water when DCM was removed. The peptide was washed further with water and dried at 30-35° C. under 15 Torr vacuum. Deprotection and purification was performed as described in the examples 2, 3 and 4.

Total yields vary from 45-65%. The procedure was repeated for each species.

Example 6

Synthesis of Protected Monocyclic Human RLX1A and RLX2A by DMSO Oxidation. General Procedure:

A.1. Cys(Mmt) Selective Removal. Partial Deprotection of RLX1A, RLX2A (FIG. 9—Compounds 21 to 22 and FIG. 10 Compounds 25 to 26)

The N- and side chain protected resin-bound peptide fragment RLX1A, obtained as described above under B1-B5 (0.005 mmol) and containing two Cys residues protected by Trt and two Cys residues protected with Mmt was washed with 5 mL NMP 4 times, 5 ml IPA 3 times and finally with 7 ml DCM 5 times to remove any NMP or other basic contaminants. The resin was then cooled to 0° C. The DCM was drained and the resin was than treated four times with a precooled at 5° C. solution of 25 mL 1.5%-TFA (this is 1.1% in figures) in DCM containing 10 equivalents triethylsilane in respect to the resin bound peptide, stirred for 5 min at 5° C. and filtered. The combined filtrates were then stirred for an additional two hours at 15° C. Pyridine was then added (1.3 equiv. in respect to TFA) to neutralize TFA. The DCM cleavage solution was then combined with the equal volume of water in respect to DCM. The resulting mixture was then distilled under reduced pressure to remove DCM (350 Torr at 28° C.). The partially at the S-Mmt residues deprotected peptide or peptide fragment precipitated out from the water when DCM was removed. The fragment was washed with water and dried at 30-35° C. under 15 Torr vacuum. The procedure was repeated to produce RLX2A.

A2. DMSO Oxidation from Free Cysteine to Monocyclic

The peptides obtained from the above described Al procedure (0.005 mmol) were each dissolved in 5 ml DMSO and stirred for 24 hours at 25° C. Then 5 ml water were added and stirred for additional 30 min. The precipitated monocyclic protected peptide was washed five times with water and dried in vacuum to constant weight (30° C., 15 Torr). Deprotection and purification were performed as described in examples 2, 3 and 4. Total yields varied from 50-70%.

This procedure is illustrated with respect to the production of RLX1A and RLX2A and may also be employed to selectively remove protecting groups on cysteine residues of RLX1B and RLX2B.

Example 7

Synthesis of Bicyclic Human RLXA1 and RLX2A and of Their Derivatives, General Procedure:

A1. By Iodine Oxidation of Protected Monocyclic RLX1A, RLX2A in Which the two Cys Residues are Side Chain Trt-Protected (FIG. 9 Compounds 22 to 23 and FIG. 10 Compounds 26 to 27).

Monocyclic protected RLX1A (0.005 mmol) with two Cys residues protected with Trt, was dissolved in 5 ml DCM/TFE (7:3). The solution was cooled at 5° C. and then 10 equiv. iodine in 5 ml DCM were added and the mixture was stirred for 1 hour. The DCM solution was then combined with 5 times its volume with 3%-sodium thiosulfate or ascorbic acid in water in respect to DCM to destroy excess iodine. This is indicated by the decolourisation of the mixture. The resulting mixture was distilled under reduced pressure to remove DCM (350 Torr at 28° C.). The protected peptide or peptide fragment precipitated out from the water when DCM was removed. The precipitated protected peptide was then washed with water and dried at 30-35° C. under 15 Torr vacuum. Deprotection and purification was performed as described in the examples 2, 3 and 4. The procedure was repeated with RLX2A. Total yields varied from 50-80%.

A2. By Iodine Oxidation of Protected Monocyclic Human RLX1A, RLX2A in Which the Two Cys Residues are Acm Protected (FIG. 11 Compounds 30 to 23 and FIG. 12 Compounds 32 to 27).

Monocyclic protected RLX1A (0.005 mmol) with two Cys residues protected with Acm, was dissolved in 5 ml AcOH/trifluoroethanol (TFE) (5:5). The solution was cooled at 5° C. and then 20 equiv. iodine in 5 ml TFE was added and the mixture was stirred for 1 hour. The solution was then combined with 5 times its volume with 3%-sodiumthiosulphate or ascorbic acid in water to destroy excess iodine. This is indicated by the decolourization of the mixture. The precipitated protected peptide was then washed with water and dried at 30-35° C. under 15 Torr vacuum. Deprotection and purification was performed as described in the examples 2, 3 and 4. The procedure was repeated with RLX2A. Total yields varied from 50-60%.

A3. By DMSO Oxidation of Monocyclic Deprotected Human RLXA1 and RLXA2, General Procedure.

Monocyclic deprotected RLX1A or RLX2A (0.005 mmol) were dissolved in 4 ml ammonium acetate buffer of pH=4. Then, 1 ml DMSO was added and the mixture was stirred at 15° C. for 24 h. From the resulting solution the bicyclic peptide was isolated after purification as described in example 4. Total yields varied from 65-85%.

A4. By DMSO Oxidation of Linear Deprotected Human RLXA1 and RLXA2, General Procedure (FIG. 13 Compounds 34 to 24, 35 and 36 and FIG. 14 Compounds 38 to 28, 39 and 40).

Deprotected linear RLX1A (0.005 mmol) was dissolved in 4 ml ammonium acetate buffer of pH=4. Then, 1 ml DMSO was added and the mixture was stirred at 15° C. for 24 h. From the resulting solution two dicyclic peptide isomer mixtures were isolated after purification as described in example 4. The procedure was repeated with RLX2A. Total yields of the pure isomers obtained varied from 60-80%.

Example 8

Synthesis of Monocyclic Human $Met(O)^{24}$-RLX1B and $Met(O)^{25}$-RLX2B General Procedure (FIG. 5 Compounds 9 to 10 and FIG. 6 Compounds 13 to 14)

Deprotected linear human $Met(O)^{24}$-RLX1B (0.005 mmol) was dissolved in 4 ml sodium glycinate buffer of pH=10.5. Then, 1 ml DMSO was added and the mixture was stirred at 15° C. for 24 h. From the resulting solution the cyclic peptide was isolated after purification using the method described in example 4. The procedure was repeated with $Met^{25}(O)$-RLX2B. The yields from three purifications averaged 45%.

Example 9

Synthesis of Human $B-Met^{24}(O)$-RLX1 $Met(O)^{24}$ by Combination of Linear RLX1A and Linear $Met(O)^{24}$-RLX1B and Synthesis of Human $B-Met(O)^{25}$-RLX2 by Combination of Linear RLX2A and Linear $Met(O)^{25}$-RLX2B; General Procedure:

Deprotected linear human RLX1A (0.006 mmol) and Met $(O)^{24}$-RLX1B $Met(O)^{25}$ (0.005 mmol) were dissolved in 4 ml sodium glycinate buffer/6-N guanidinium hydrochloride (4:1) of pH=10.5. Then, 1 ml DMSO was added during a period of 12 hours and the mixture was stirred at 15° C. for additional 4 h. From the resulting solution $Met(O)^{24}$-RLX1 $Met(O)^{25}$ was isolated after purification using the method described in example 4. $B-Met(O)^{25}$-RLX2 was produced using the same procedure starting from linear RLX2A and $Met(O)^{25}$-RLX2B. The yields averaged over three runs: $B-Met(O)^{25}$-RLX1 37% and $B-Met(O)^{24}$-RLX2 35%.

Example 10

Synthesis of Human $B-Met^{24}(O)$-RLX1 by Combination of Linear RLX1A and Cyclic $Met(O)^{24}$-RLX1B and Synthesis of Human $B-Met(O)^{25}$-RLX2 by Combination of Linear RLX2A and Cyclic $Met(O)^{25}$-RLX2B, General Procedure:

Deprotected linear RLX1A (0.005 mmol) and cyclic Met $(O)^{24}$-RLX1B $Met(O)^{25}$ (0.005 mmol) were dissolved in 4 ml sodium glycinate buffer/6-N guanidinium hydrochloride (4:1) at pH 10.5 and stirred for five hours at 15° C. Then, 1 ml DMSO was added during a period of 12 hours and the mixture was stirred at 15° C. for additional 4 h. From the resulting solution $Met(O)^{24}RLX1$ was isolated after purification using the method described in example 4. The procedure was repeated to produce human $B-Met(O)^{25}$-RLX2 by combination of linear RLX2A and cyclic $Met(O)^{25}$-RLX2B. The yields from three purifications averaged: $B-Met(O)^{25}$-RLX1 32% and $B-Met(O)^{24}$-RLX2 67% based on the applied chain B.

Example 11

Synthesis of Human $B-Met^{24}(0)$-RLN1 and $B-Met^{25}(0)$-RLN2 by Combination of Monocyclic RLN1A or RLN2A and Linear $Met^{24}(0)$-RLN1B and $Met^{25}0)$-RLN2B; General Procedure:

Deprotected monocyclic human linear RLN1A or RLN2A (0.006 mmol) and $Met^{24}$ (0)-RLN1B or $Met^{25}(0)$-RLN2B (0.005 mmol) were dissolved in 4 ml sodium glycinate buffer/6-N guanidinium hydrochloride (4:1) of pH=10.5. Then, 1 ml DMSO was added during a period of 12 hours and the mixture was stirred at 15° C. for additional 4 h. From the resulting solution $Met^{24}(0)$-RLN1B or $Met^{25}(0)$-RLN2B were isolated after purification as described in example 4.

The yields averaged over three runs: B-Met$^{24}$(0)-RLN1 32% and B-Met$^{25}$(0)-RLN2 36%.

Example 12

Synthesis of Hum B-Met$^{24}$(0)-RLN1 and B-Met$^{25}$(0)-RLN2 by Combination of Monocyclic RLN1A or RLN2A and Cyclic Met$^{24}$(0)-RLN1B and Met$^{25}$(0)-RLN2B General Procedure.

Deprotected monocyclic human RLN1A or RLN2A (0.006 mmol) and cyclic Met$^{24}$(0)-RLN1B or Met$^{25}$(0)-RLN2B (0.005 mmol) were dissolved in 4 ml sodium glycinate buffer/6-N guanidinium hydrochloride (4:1) of pH=10.5. Then, 1 ml DMSO was added during a period of 12 hours and the mixture was stirred at 15° C. for additional 4 h. From the resulting solution Met$^{24}$(0)-RLN1B or Met$^{25}$(0)-RLN2B were isolated after purification as described in example 4.

The yields averaged over three runs: B-Met$^{24}$(0)-RLN1 35% and B-Met$^{25}$(0)-RLN2 38%.

Example 13

Synthesis of Human Met(O)$^{24}$-RLX1 Met(O)$^{25}$-RLX2 by Combination of Bicyclic RLX1 and Linear Met(O)$^{24}$-RLX1B and Synthesis of Human Met(O)$^{25}$-RLX2 by Combination of Bicyclic RLX2 and Linear Met(O)$^{25}$-RLX2B; General Procedure: (FIG. 16).

Deprotected bicyclic RLX1A (0.005 mmol) and linear Met(O)$^{24}$-RLX1B Met(O)$^{25}$(0.1 mmol) were dissolved in 4 ml sodium glycinate/6-N guanidiniumhydrochloride (4:1) buffer at pH 10.5 and stirred for one hour at 15° C. Then, 1 ml DMSO was added during a period of 12 hours and the mixture was stirred at 24° C. for additional 4 h. From the resulting solution Met(O)$^{25}$-RLX1 were isolated after purification using the method described in example 4. The procedure was repeated to produce human Met(O)$^{25}$-RLX2 by combination of bicyclic RLX2 and linear Met(O)$^{25}$-RLX2B. The yields from three purifications averaged: B-Met(O)$^{25}$-RLX1 64% and B-Met(O)$^{24}$-RLX2 76% based on the applied chain B.

Example 14

Synthesis of Human B-Met(O)$^{24}$RLX1 by Combination of Bicyclic RLX1A and Cyclic Met(O)$^{24}$-RLX1B and Synthesis of B-Met(O)$^{25}$RLX2 by Combination of Bicyclic RLX2A and Cyclic Met(O)$^{25}$RLX2B; General Procedure (FIG. 17).

Deprotected bicyclic RLX1A (0.011 mmol) and cyclic Met(O)$^{24}$-RLX1B or Met(O)$^{25}$-RLX2B (0.01 mmol) were dissolved in 15 ml sodium glycinate/6-N guanidiniumhydrochloride (4:1) buffer at pH 10.5. Then, a solution of 0.001 mmol thiophenol in 3 mL THF was added and the mixture was stirred at 15° C. for 24 h. From the resulting solution Met(O)$^{24}$-RLX1 or Met(O)$^{25}$-RLX2 were isolated after purification using the method described in example 4. The procedure was repeated to produce Met(O)$^{25}$-RLX2B from bicyclic RLX2A and cyclic Met(O)$^{25}$RLX2B. The yields from three purifications averaged: B-Met(O)$^{24}$RLX1 68%, B-Met(O)$^{25}$RLX2 72% based on the applied chain B.

Example 15

Synthesis of Human RLX1, RLX2, RLX1B, RLX2B, Cyclic RLX1B and Cyclic RLX2B by the Reduction of B-Met(O)$^{24}$RLX1, B-Met(O)$^{25}$RLX2, Met(O)$^{24}$RLX1B, Met(O)$^{25}$RLX2B, Cyclic Met(O)$^{24}$RLX1B and Cyclic Met(O)25B Respectively with Ammonium Iodide, General Procedure:

This procedure was carried out with each Met(O) containing peptide or protein analogue of RLX1, RLX2, RLX1B, RLX2B, cyclic RLX1B and cyclic RLX2B. 0.01 mmol of the Met(O) analogue was dissolved in 25 ml 90%-TFA in water. Then, 1 mmol of ammonium iodide was added and the mixture was stirred at 24° C. for 15 min. From the resulting solution the desired product (RLX1, RLX2, RLX1B, RLX2B, cyclic RLX1B cyclic RLX2B) was isolated after purification by HPLC using the method described in the example 4. The yields from three purifications averaged: RLX1 91%, RLX2 89%, RLX1B 62%, RLX2B 64%, cyclic RLX1B 88% and cyclic RLX2B 81%.

While a number of exemplary embodiments, aspect and variations have been provided herein, those of skill in the art will recognize certain modification, permutations, additions and combinations and certain sub-combinations of the embodiments, aspect and variations. It is intended that the following claims are interpreted to include all such modifications, permutations, additions and combinations and certain sub-combinations of the embodiments, aspects and variations are within their scope. The entire disclosures of all documents cited throughout this application are incorporated herein by reference in their entirety.

What is claimed:

1. A synthetically produced, isolated human relaxin 1 and a pharmaceutically acceptable salt, wherein the relaxin 1 contains one methionine sulphoxide residue wherein the methionine sulphoxide is a Met(O)$^{24}$-RLX1B or Met(O)$^{25}$ relaxin 1.

2. A method for the treatment of renal fibrosis, kidney weight gain, cancer and cardiovascular disease in a patient, the method comprising administering of the isolated human relaxin 1 as defined in claim 1 and a pharmaceutically acceptable salt, to a patient in need thereof.

3. A pharmaceutical composition comprising a synthetic polypeptide as defined in claim 1, and a pharmaceutically acceptable carrier.

4. A biologically active, synthetic relaxin containing one methionine sulphoxide residues and a pharmaceutically acceptable salt, wherein the methionine sulphoxide is a Met(O)$^{24}$-RLX1B or Met(O)$^{25}$ relaxin 1.

5. The isolated synthetic human relaxin according to claim 4 selected from:
  i) human Met(O)$^{24}$-relaxin 1 having a sequence as illustrated in FIG. 3;
  ii) human Met(O)$^{25}$-relaxin 2 having a sequence as illustrated in FIG. 4; and
  iii) a pharmaceutically acceptable salt of i) or ii).

6. A synthetic chimeric polypeptide comprising a polypeptide sequence of human Met(O)$^{24}$-relaxin 1, human Met(O)$^{25}$-relaxin 2 as defined in claim 5.

7. The synthetic chimeric polypeptide according to claim 6 comprising i) RLX1A and RLX2B or Met(O)RLX2B or ii) RLX2A and RLX1B or Met(O)RLX2B.

8. A synthetic chimeric polypeptide comprising:
a polypeptide sequence of synthetic relaxin as defined in claim 4.

9. An isolated synthetic polypeptide comprising a polypeptide sequence of a synthetic relaxin A-chain, a synthetic relaxin B-chain comprising a single methionine oxide analogue.

10. The isolated synthetic polypeptide according to claim 9 selected from the group consisting of RLX1A, RLX2A, RLX1B, RLX2B, Met(O)$^{24}$-RLX1B and Met(O)$^{25}$-RLX2B.

* * * * *